(12) United States Patent
Heneveld et al.

(10) Patent No.: US 12,390,213 B1
(45) Date of Patent: Aug. 19, 2025

(54) SYSTEMS, APPARATUS AND METHODS FOR PASSING SUTURE THROUGH SOFT TISSUE

(71) Applicant: Passer Stitch, LLC, Whitmore, CA (US)

(72) Inventors: Scott Heneveld, Whitmore, CA (US); John Valadez, Agua Dulce, CA (US); Christopher Morris, Santa Clarita, CA (US); Justin Anderson, Henderson, NV (US); Brad Topper, Santa Clarita, CA (US)

(73) Assignee: Passer Stitch, LLC, Henderson, NV (US)

( * ) Notice: Subject to any disclaimer, the term of this patent is extended or adjusted under 35 U.S.C. 154(b) by 31 days.

(21) Appl. No.: 18/623,903

(22) Filed: Apr. 1, 2024

Related U.S. Application Data

(60) Provisional application No. 63/602,605, filed on Nov. 26, 2023, provisional application No. 63/456,513, filed on Apr. 2, 2023.

(51) Int. Cl.
*A61B 17/04* (2006.01)
*A61B 17/00* (2006.01)
*A61B 17/06* (2006.01)
*A61B 17/29* (2006.01)

(52) U.S. Cl.
CPC ............. *A61B 17/0469* (2013.01); *A61B 2017/00367* (2013.01); *A61B 2017/047* (2013.01); *A61B 2017/2925* (2013.01); *A61B 2017/2926* (2013.01)

(58) Field of Classification Search
CPC ........ A61B 2017/047; A61B 2017/294; A61B 2017/00367; A61B 2017/2925; A61B 2017/2926; A61B 2017/2936; A61B 2017/2933; A61B 2017/2934; A61B 2017/2944; A61B 17/0469; A61B 17/0483; A61B 17/0482; A61B 17/06004; A61B 17/06066
See application file for complete search history.

(56) References Cited

U.S. PATENT DOCUMENTS

| | | | |
|---|---|---|---|
| 10,383,621 B2 | 8/2019 | Gregoire et al. | |
| 2008/0208221 A1* | 8/2008 | Murray | A61B 17/0625 606/145 |
| 2014/0188136 A1* | 7/2014 | Cournoyer | A61B 17/0401 606/144 |
| 2014/0276981 A1* | 9/2014 | Hendricksen | A61B 17/0483 606/144 |

(Continued)

*Primary Examiner* — Tuan V Nguyen
(74) *Attorney, Agent, or Firm* — Francis Law Group

(57) ABSTRACT

An apparatus for passing suture through biological tissue. The apparatus including a jaw mechanism adapted to grasp the tissue, a needle assembly having a needle, a jaw articulation system for inducing axial articulation of the jaw mechanism, a needle articulation system for inducing articulation of the needle, a suture control system for controlling ensnarement and release of a suture, and a multifunction actuation system having an actuation trigger. The multifunction actuation system adapted to sequentially induce the axial articulation of the jaw mechanism, the ensnarement of the suture and articulation of the needle during a single continuous rotation of the trigger.

15 Claims, 32 Drawing Sheets

(56) References Cited

U.S. PATENT DOCUMENTS

| | | | |
|---|---|---|---|
| 2014/0296880 A1* | 10/2014 | Heneveld | A61B 17/0469 606/144 |
| 2017/0172565 A1 | 6/2017 | Heneveld | |
| 2018/0235601 A1 | 8/2018 | Malkowski et al. | |
| 2020/0093479 A1 | 3/2020 | Murillo et al. | |
| 2020/0360012 A1 | 11/2020 | Heneveld | |
| 2021/0000463 A1 | 1/2021 | Murillo et al. | |

* cited by examiner

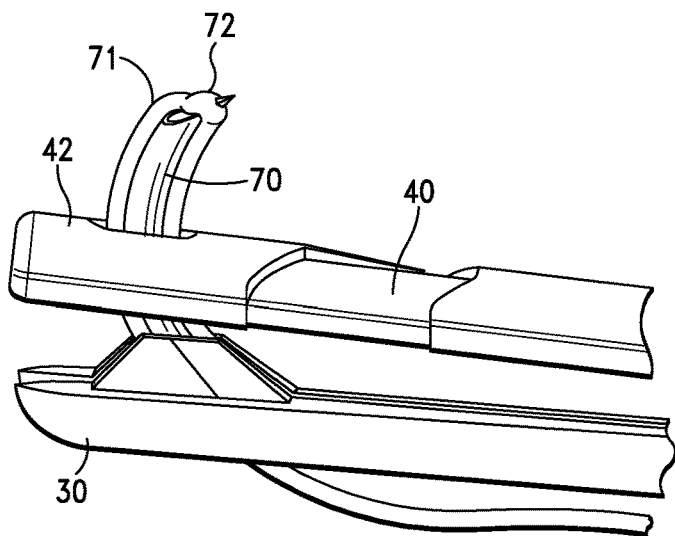
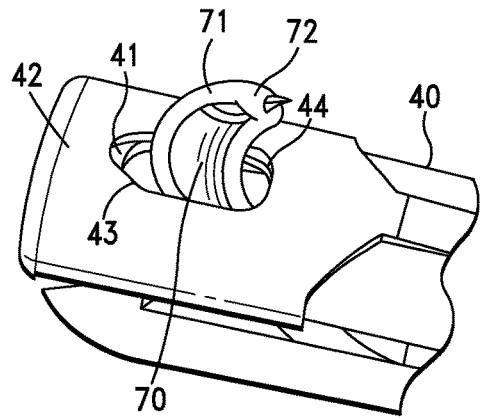
FIG. 6A  FIG. 6B
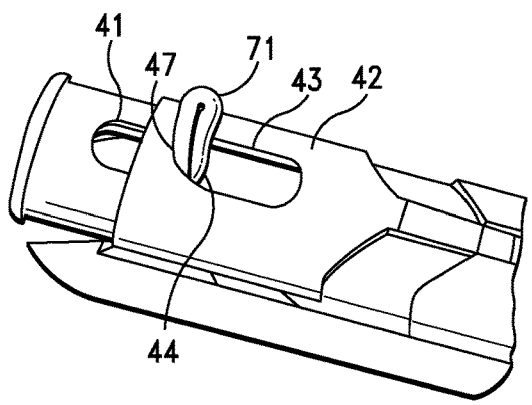
FIG. 6C
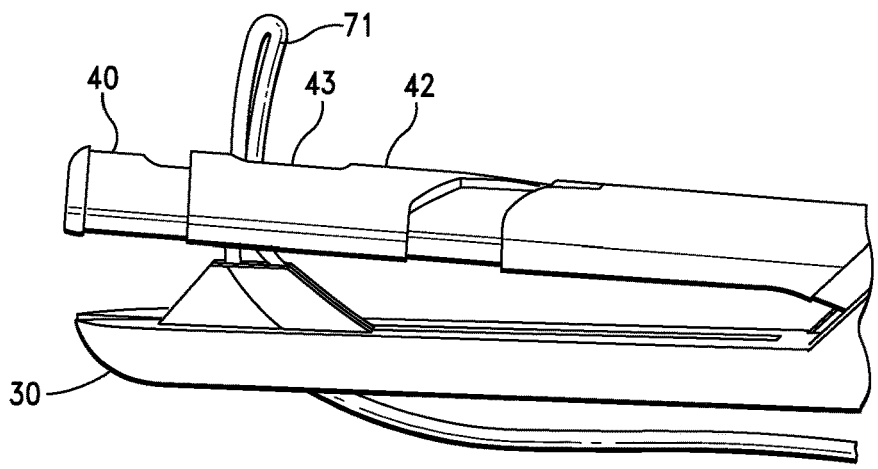
FIG. 6D

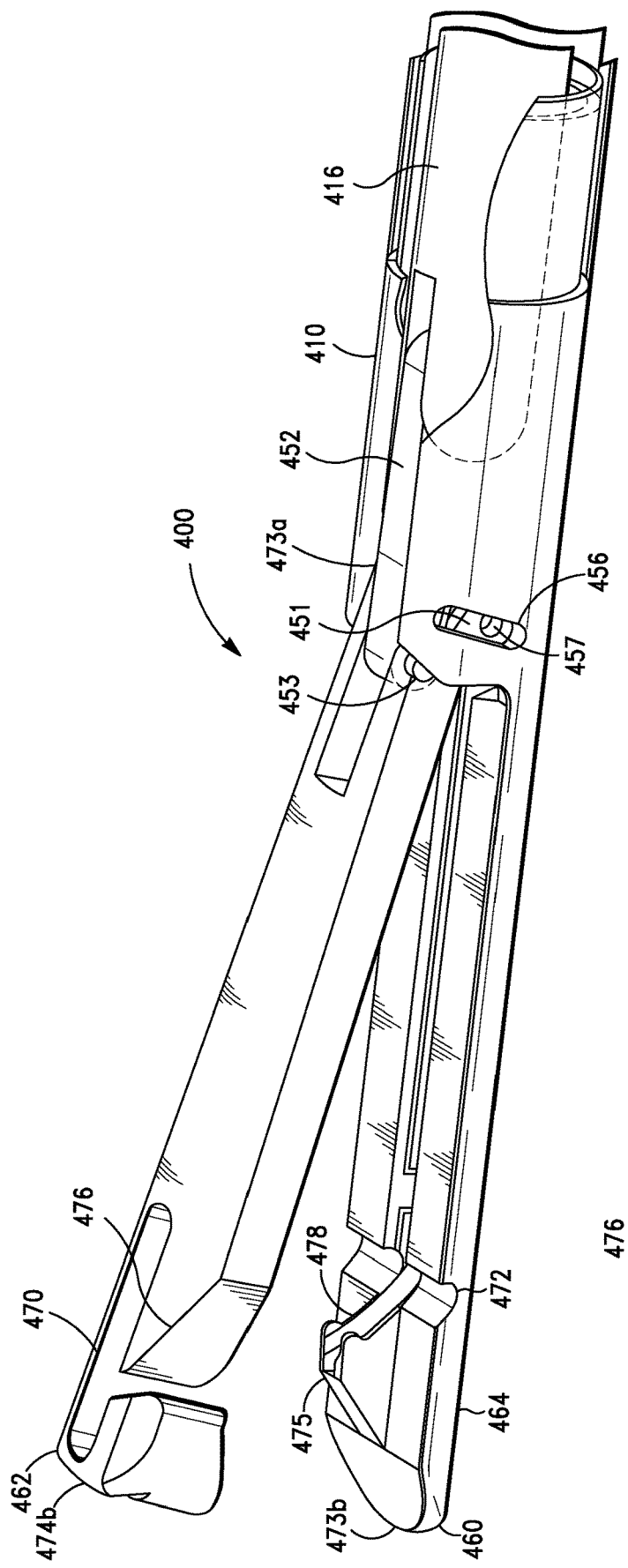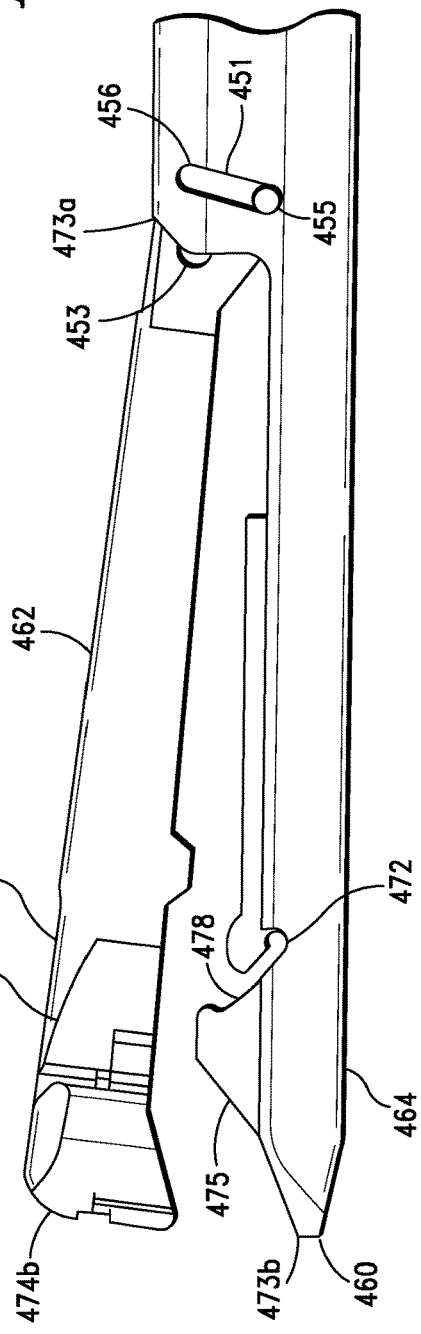
FIG. 24A
FIG. 24B

Synchronized Suture Passing Device Functions

| Trigger Actuation | | Jaw Articulation System | Suture Control System | Needle Articulation System |
|---|---|---|---|---|
| Stage 1 | Default State–A° | forward gear driven | stationary (in dwell) | stationary (in dwell) |
| Stage 2 | A°–B° | stationary (in dwell) | gear driven retracted | stationary (in dwell) |
| Stage 3 | B°–Fully Actuated | stationary (in dwell) | stationary (in dwell) | forward gear driven |
| Stage 4 | Fully Actuated–B° | stationary (in dwell) | stationary (in dwell) | gear driven retracted |
| Stage 5 | B°–A° | stationary (in dwell) | forward gear driven | spring retracted |
| Stage 6 | A°–Default State | gear driven retracted | stationary (in dwell) | spring retracted |

TRIGGER ACTUATION (CLOSING): Stages 1–3
TRIGGER ACTUATION (RETURNING): Stages 4–6

*FIG. 30*

Suture Passing Device Functions
With Manual Suture Release System

| | | AUTOMATIC FUNCTIONS | | INDEPENDENT FUNCTIONS |
| --- | --- | --- | --- | --- |
| | ACTUATION TRIGGER | Needle Articulation System | Jaw Articulation System | MANUALLY ACTIVATED Suture Release System |
| Stage 1 | 0°–A° | stationary (in dwell) | forward gear driven | |
| Stage 2 | A°–B° | stationary (in dwell) | stationary (in dwell) | |
| Stage 3 | B°–C° | forward gear driven | stationary (in dwell) | |
| Stage 4 | C°–B° | gear driven retracted | stationary (in dwell) | |
| Stage 5 | B°–A° | spring retracted | stationary (in dwell) | |
| Stage 6 | A°–0° | spring retracted | gear driven retracted | |

TRIGGER ACTUATION (CLOSING): Stages 1–3
TRIGGER ACTUATION (RETURNING): Stages 4–6

*FIG. 36*

SYSTEMS, APPARATUS AND METHODS FOR PASSING SUTURE THROUGH SOFT TISSUE

CROSS-REFERENCES TO RELATED APPLICATIONS

This application claims the benefit of U.S. Provisional Application No. 63/456,513, filed on Apr. 2, 2023 and U.S. Provisional Application No. 63/602,605, filed on Nov. 26, 2023.

FIELD OF THE INVENTION

As is well established, suturing is a fundamental aspect of many surgical procedures; particularly, surgical procedures that involve suturing soft tissues, such as fascia, muscles, ligaments, and tendons. The process of suturing soft tissue in a surgical site often involves employing a suture passing device to pass a suture through the soft tissue in a particular pattern to secure portions of soft tissue together or one or more portions of soft tissue to an implantable device.

BACKGROUND OF THE INVENTION

As is well established, suturing is a fundamental aspect of many surgical procedures; particularly, surgical procedures that involve suturing soft tissues, such as fascia, muscles, ligaments, and tendons. The process of suturing soft issue in a surgical site often involves employing a suture passing device to pass a suture through the soft tissue in a particular pattern to secure portions of soft tissue together or one or more portions of soft tissue to an implantable device.

Conventional suture passing devices, such as the device disclosed in U.S. Pat. No. 10,383,621 to Gregoire, et al., typically include an elongated shaft and a low-profile distal clamping mechanism to allow the clamping mechanism to be deployed in a surgical site via cannulas in less invasive surgical procedures. The conventional suture passing devices also typically include a jaw mechanism with top and bottom jaw members that are sized and configured to clamp onto soft tissue and fixate the soft tissue for passage of a suture therethrough.

Conventional suture passing devices are also often designed and configured to position and secure a portion of a suture proximate to the distal end of a jaw mechanism. The system for capturing a suture between the top and bottom jaw members of such devices and through soft tissue typically includes a bendable needle, which advances into and through the elongated shaft and through an opening that is disposed on the distal end of the bottom jaw member.

Most bendable needles of suture passing devices include suture capture means proximate to the distal end of the needle for capturing a portion of suture, which captures the portion of suture and allows the captured portion of suture to be drawn through soft tissue by an operator.

Some conventional suture passing devices also include suture retainment means that is adapted and configured to retain a portion of suture (usually in a top jaw member of a jaw mechanism) after the portion of suture has been drawn through soft tissue for manipulation by the passing device in a surgical site, e.g., forming a particular suture pattern.

Although conventional suture passing devices can be employed to suture soft tissues in a surgical site with some success, there are numerous drawbacks and disadvantages associated with the use of conventional suture passing devices, which include difficulties associated with controlling the direction of suture passage and manipulating a portion of suture in a confined surgical site, and an inability to pass suture through delicate or sensitive soft tissues.

A further disadvantage associated with the use of conventional suture passing devices is that such devices do not provide an operator with optimal control over articulation of a jaw mechanism or needle articulation or suture retainment and release.

Although some conventional suture passing devices provide means for jointly articulating a jaw and needle, such as the device disclosed in U.S. Pat. No. 10,383,621, operators of such devices typically have minimal, if any, control over the individual timing of the jaw and needle articulation.

Such devices; particularly, the suture passing device disclosed in U.S. Pat. No. 10,383,621, are also devoid of any means for controlling the timing of suture retainment and release.

A major drawback and disadvantage associated with the inability to control the timing of suture retainment and release is that an operator has minimal control over suture tension in a surgical site, which can, and most instances will, adversely affect the engagement of the suture to soft tissue, and limits the types of soft tissue that can be sutured by the device.

A further disadvantage associated with conventional suture passing devices that are devoid of any means for controlling the timing of suture retainment and release is that the types of suture patterns that can be created with the devices are often limited.

There is thus a need for improved suture passing systems, apparatus and methods that substantially reduce or eliminate the disadvantages and drawbacks associated with conventional suture passing systems, apparatus and methods.

It is thus an object of the present invention to provide improved suture passing systems, apparatus and methods that substantially reduce or eliminate the disadvantages and drawbacks associated with conventional suture passing systems, apparatus and methods.

It is another object of the present invention to provide improved suture passing systems, apparatus and methods that provide optimal control of tissue engagement, needle articulation and suture retention and release.

It is another object of the present invention to provide improved suture passing systems, apparatus and methods that provide synchronized control of tissue engagement, needle articulation and suture retention and release with a single motion of a hand actuator requiring a single hand to actuate and thus allows the operator's other hand to be free at all times for manipulation and handling of other instrumentation (i.e., cannula, camera, etc.).

It is another object of the present invention to provide improved suture passing systems, apparatus and methods that provide automated control of suture retention and release with minimal complexity.

It is another object of the present invention to provide improved suture passing systems, apparatus and methods that provide independent manual means for releasing a tissue after retainment.

It is another object of the present invention to provide improved suture passing systems, apparatus and methods that facilitate suture passage into and through a myriad of soft tissue types.

It is another object of the present invention to provide improved suture passing systems, apparatus and methods that facilitate suture passage into and through biological tissue structures having a wide range of thicknesses.

It is another object of the present invention to provide improved suture passing systems, apparatus and methods that provide enhanced suture manipulation in a surgical site.

It is another object of the present invention to provide improved suture passing systems, apparatus and methods that can be readily employed to pass suture without collateral damage to extraneous soft tissue and bone structures.

It is another object of the present invention to provide improved suture passing systems, apparatus and methods that reduce the time required to conduct suturing procedures and, thereby, attendant risks to a patient.

SUMMARY OF THE INVENTION

The present invention is directed to systems, apparatus and methods for passing suture through biological tissue. In one embodiment of the invention there is thus provided an apparatus for passing suture through biological tissue, the apparatus comprising:
- a jaw mechanism adapted to grasp biological tissue, the jaw mechanism comprising top and bottom jaw members, the top jaw member adapted to axially articulate with respect to the bottom jaw member;
- a needle assembly comprising a needle, the needle comprising a tissue piercing distal end configured to releasably engage a suture;
- a jaw articulation system adapted to induce and control the axial articulation of the top jaw member with respect to the bottom jaw member;
- a suture control system comprising a suture engagement ribbon, the suture control system adapted to induce and control engagement and release of the suture engagement ribbon to the suture;
- a needle articulation system adapted to induce and control articulation of the needle and, thereby, the needle engagement to the suture; and
- a multifunction actuation system, the multifunction actuation system comprising an actuation trigger, the actuation trigger adapted to rotationally articulate from a default position to a fully actuated position, the default position comprising 0° rotation of the actuation trigger, the multifunction actuation system adapted to control the jaw articulation system, suture control system and needle articulation system,
- the control of the jaw articulation system, suture control system and needle articulation system comprising synchronized axial articulation of the top jaw member with respect to the bottom jaw member, the suture engagement and release, and the articulation of the needle during a first single continuous rotational articulation of the trigger, the first single continuous rotational articulation of the trigger comprising rotational articulation from the default position to the fully actuated position.

In a preferred embodiment, the control of the jaw articulation system, the suture control system and the needle articulation system further comprises synchronized articulation of the needle, the suture engagement and release, and the axial articulation of the top jaw member with respect to the bottom jaw member during a second single continuous rotational articulation of the trigger, the second single continuous rotational articulation of the trigger comprising rotational articulation from the fully actuated position to the default position.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 6A is a partial side view of the tubular needle that is extended to engage and carry the suture through the aperture of the jaw mechanism and pawl, in accordance with the invention;

FIG. 6B is a perspective view of the tubular needle that is extended to carry the suture through the aperture of the jaw mechanism and pawl shown in FIG. 6A, in accordance with the invention;

FIG. 6C is a perspective view of the suture captured by the pawl shown in FIG. 6A, in accordance with the invention;

FIG. 6D is a side plan view of the suture captured by the pawl shown in FIG. 6A, in accordance with the invention;

FIG. 24A is a perspective view of a jaw mechanism of the suture passing device shown in FIG. 23, in accordance with the invention;

FIG. 24B is a partial side plan view of the jaw mechanism shown in FIG. 24A, in accordance with the invention;

FIG. 30 is a table reflecting the states of the jaw articulation system, suture control system, and needle articulation system throughout various stages of actuation of the suture passing device shown in FIG. 23, in accordance with the invention;

FIG. 36 is a table reflecting the automatic functions, i.e., states of the jaw articulation system and needle articulation system of the suture passing device shown in FIG. 31A throughout various stages of actuation, and the manual function, i.e., suture release, of the suture passing device, in accordance with the invention.

DETAILED DESCRIPTION OF THE PREFERRED EMBODIMENT

Figure 1A:
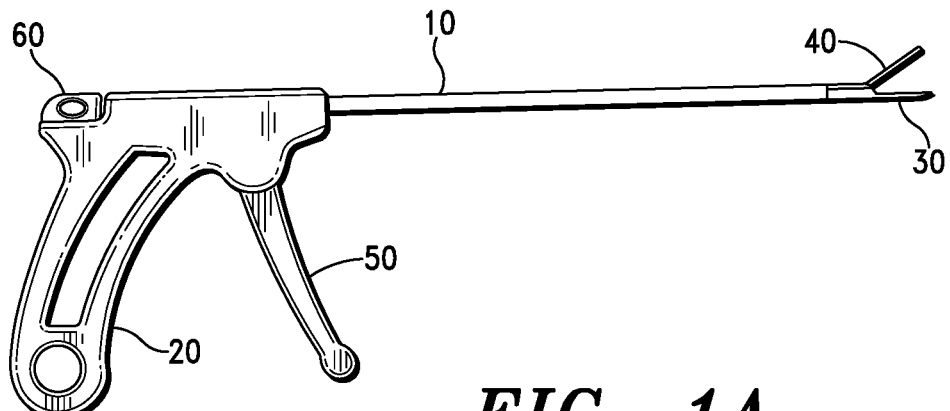
FIGS. 1A-1C are side plan views of an embodiment of a suture passing device in various stages of deployment, in accordance with the invention.

Before describing the present invention in detail, it is to be understood that this invention is not limited to particularly exemplified systems, apparatus, structures or methods as such may, of course, vary. Thus, although a number of systems, apparatus, structures and methods similar or equivalent to those described herein can be used in the practice of the present invention, the preferred systems, apparatus, structures and methods are described herein.

It is also to be understood that, although the present invention is described and illustrated in connection with endoscopic procedures, the invention is not limited to such procedures. According to the invention, the apparatus, systems and methods of the invention can also be employed in connection with a multitude of other surgical procedures, including open surgical procedures.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an active" includes two or more such actives and the like.

Further, ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10", as well as "greater than or equal to 10" is also disclosed.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The words used in the description to describe the invention and its various embodiments are to be understood not only in the sense of their commonly defined meanings, but to include by special definition in this specification the generic structure, material or acts of which they represent a single species.

The present invention relates generally to systems and methods for the driving of a needle or suture through or into body tissue (typically, the needle will be affixed to a suture that remains in the tissue) using a cannula, introducer or other minimally invasive means. The methods and devices described herein can be used in any number of medical procedures, including but not limited to, approximating tissue (e.g., bring separated tissue together), ligating tissue (e.g., encircling or tying off), and fixating of tissue (attaching tissue to another structure or different tissue or an implantable device).

Definitions

The terms "tissue", "soft tissue" and "biological tissue" are used interchangeably herein, and mean and include mammalian biological tissue, such as, by way of example, human abdominal tissue.

The term "biological cavity", as used herein, means and includes any cavity or space in a mammalian tissue structure.

The term "surgical site", as used herein, means and includes any space or region in a mammalian tissue structure where a surgical procedure is conducted.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "endoscopy", as used herein, means and includes any minimally invasive surgical procedure conducted through at least one opening in a subject's body, including, but not limited to arthroscopy, laparoscopy, hysteroscopy and the like.

The terms "one configuration," "one embodiment," "one aspect," and "a configuration," "an embodiment" and "an aspect," as used herein, means that a particular feature, structure, or characteristic described in connection with the configuration may be included in at least one configuration and not that any particular configuration is required to have a particular feature, structure or characteristic described herein unless set forth in the claim.

The phrase "in one configuration" or similar phrases employed herein do not necessarily refer to the same configuration and, unless specifically stated, do not limit the inclusion of a particular element of the invention to a single configuration. The element may thus be included in other, or all configurations discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all of the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present disclosure is directed to devices and methods for passing suture through biological tissue; particularly, biological tissues that are accessed via an endoscopic procedure.

As is well known in the art, both open and endoscopic surgical procedures often require sutures to ligate, join or otherwise treat tissue. Generally, suture needles with attached suture strands are grasped either manually or by forceps and passed through the desired work site so a knot can be tied. Although such surgical procedures are fairly uncomplicated in open surgery procedures where most suture sites are readily accessible, surgeons must often use auxiliary devices to grasp the suture strands and pass them through desired tissue in endoscopic procedures where access to a desired suture site is not readily available.

Referring now to FIG. 1A, there is illustrated one embodiment of a suture passing device, or instrument of the present invention. As illustrated in FIG. 1A, the suture passing device comprises an elongated tubular body 10, a hand grip 20, a tip 30, a jaw mechanism 40, an actuator 50 and a needle assembly 60.

Figure 1B:
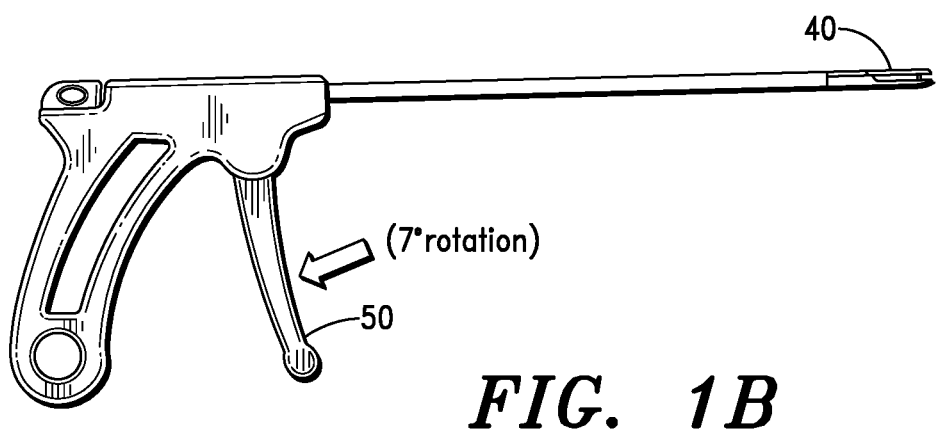
Figure 1C:
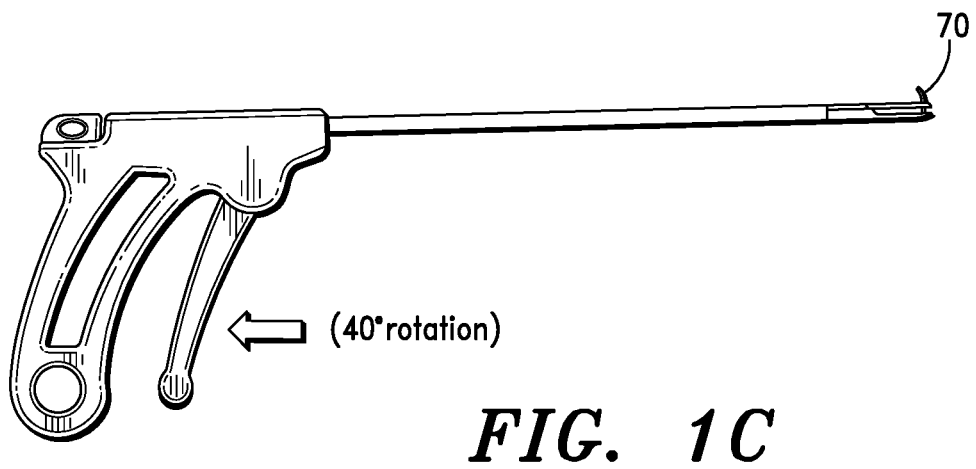

According to the invention, with actuator 50, a surgeon can seize and maintain tissue by movement of the jaw mechanism 40 against tip 30, as shown in FIG. 1B. Using actuator 50, a surgeon can also deploy a tubular needle 70 carrying a suture 71 through tissue, as shown in FIG. 1C and described below.

Figure 2A:
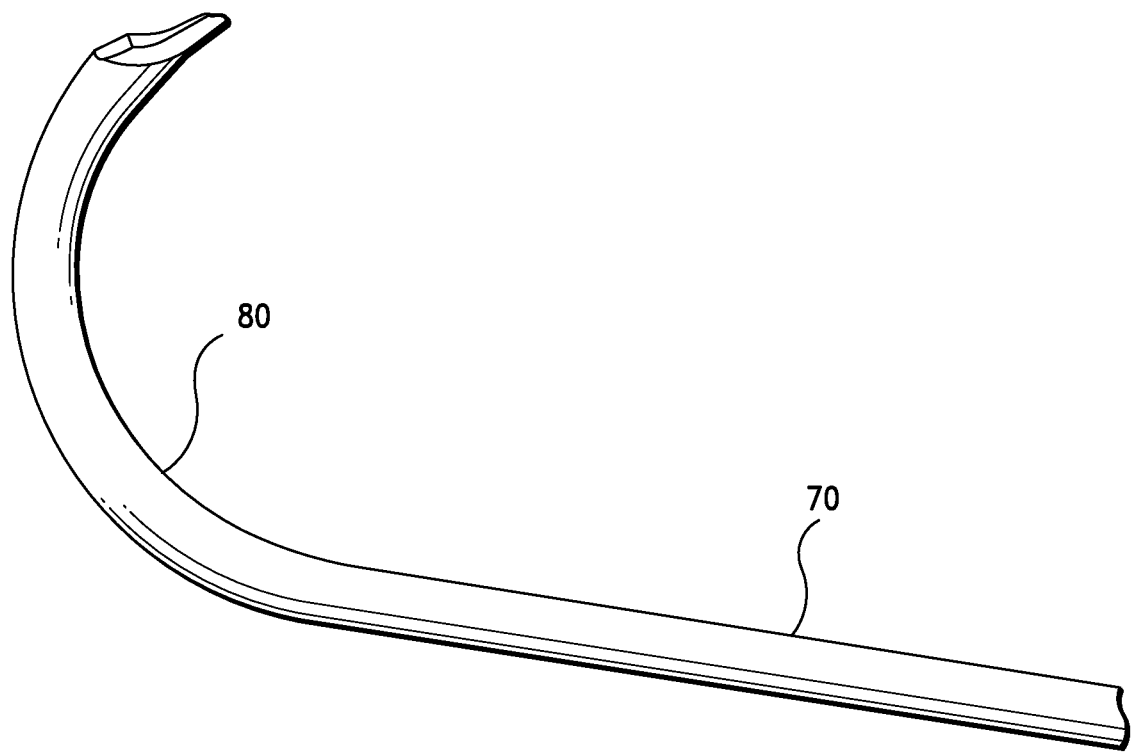
FIG. 2A is a side plan view of a notch-less tubular needle comprising a preformed memory shape, in accordance with the invention.

Referring now to FIG. 2A, there is illustrated one embodiment of a needle of the invention, i.e., a notchless tubular needle 70, in its natural state.

As used throughout the specification, the term "notchless" shall refer to the absence of notches, slots, eyelets, or other such transverse openings for receiving suture as typically formed in needles of prior art suture passers.

According to the invention, the needle 70 can also comprise a solid structure.

As illustrated in FIG. 2A, the distal end 80 of the needle 70 is formed in a non-straight geometry.

Figure 2B:
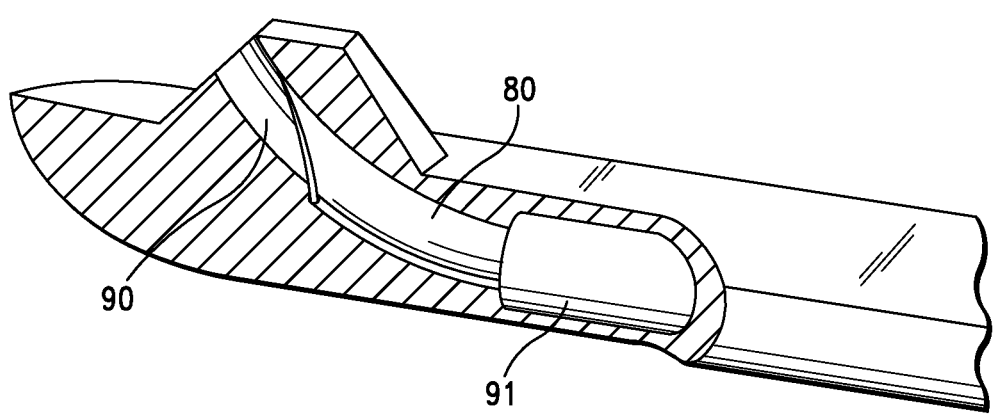
FIG. 2B is a side plan partial sectional view of a preformed tubular needle in a retracted, constrained state, in accordance with the invention.

As illustrated in FIG. 2B, the needle 70 comprises a formed end 80 sheathed in a constraining channel 91. In a preferred embodiment, the needle channel 91 also includes a curvilinear portion 90, or guide-path, which approximates the same geometry curve as the distal end 80 of the needle 70, thereby facilitating the consistent return of the needle 70 to its preformed curved shape each time the needle 70 exits the channel.

According to the invention, the constrained state needle 70 contained in the needle assembly 60 is loaded into the handle end of the elongated tubular body 10 and advanced through a track in the tubular body 10.

FIG. 1A illustrates the hand grip 20 and actuator 50 of the suture passing device, which, as set forth in Applicant's Co-pending U.S. application Ser. No. 17/891,328, provide articulation of jaw 40 relative to tip 30.

Figure 3A:
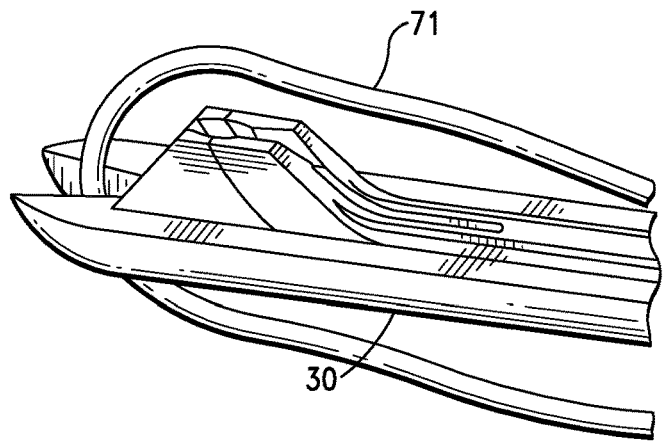
FIG. 3A is a perspective view of a lower jaw or tip of the device shown in FIG. 1A and a suture prior to loading in the tip, in accordance with the invention.
Figure 3B:
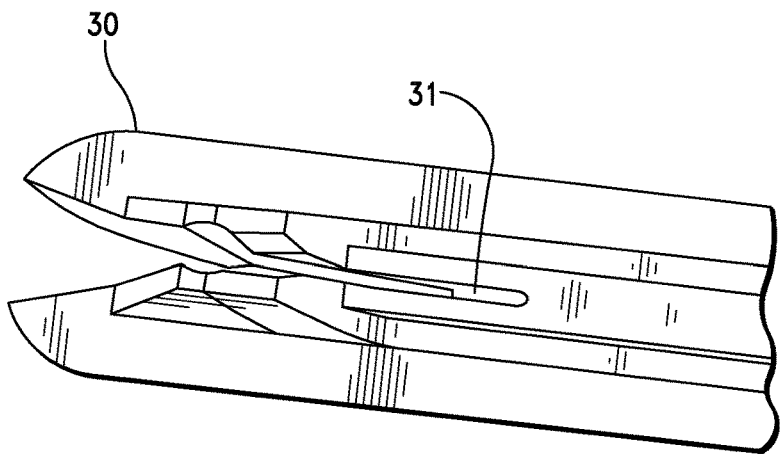
FIG. 3B is another perspective view of the tip shown in FIG. 3A showing the slot formed in the tip, in accordance with the invention.

As set forth in Co-pending U.S. application Ser. No. 17/891,328 and illustrated in FIGS. 3A and 3B, a loop of suture 71 is loaded into distal end of tip 30 with slot 31. According to the invention, the slot 31 facilitates spring action for gripping the loop of suture 71 when the loop of suture 71 is guided into the tip 30.

Figure 3C:
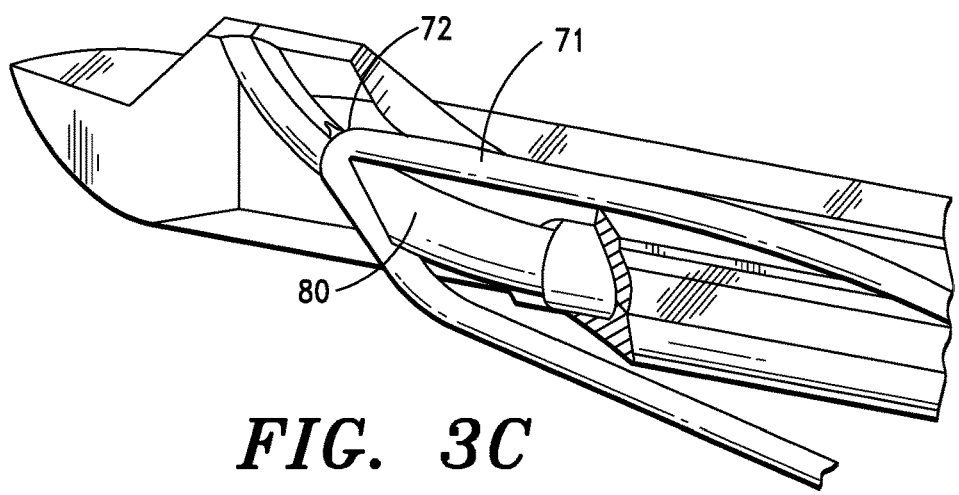
FIG. 3C is a perspective partial sectional view of the tip, tubular needle, and suture shown in FIG. 3A, in accordance with the invention.

In one embodiment of the invention, illustrated in FIG. 3C, tubular needle 70 pierces the loop of suture 71 and, thereby, creates a bifurcation 72 in the suture 71.

According to the invention, when additional force is applied to the suture 71, the bifurcation 72 advances along the shaft of the needle 70.

Figure 4A:
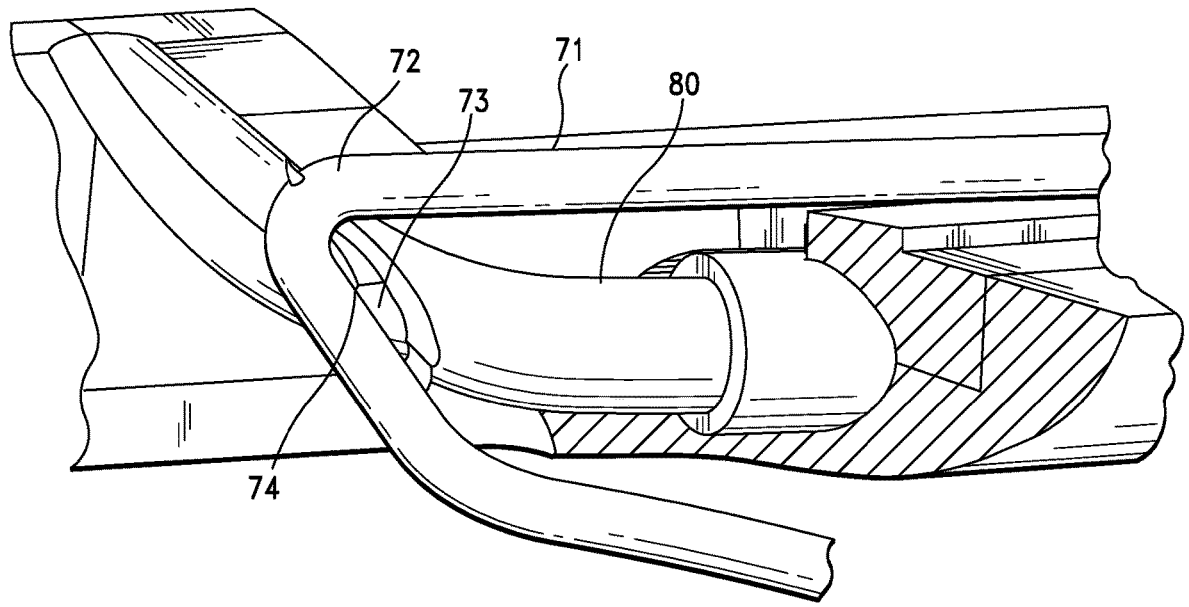
FIG. 4A is a perspective partial sectional view of the tip and tubular needle shown in FIG. 3A showing a cleat member engaged to the suture, in accordance with the invention.

As further set forth in Co-pending U.S. application Ser. No. 17/891,328 and illustrated in FIG. 4A, to prevent the bifurcation 72 from advancing along the shaft of the tubular needle 70, in some embodiments, a prong cleat 73 is positioned in the tubular needle 70 and adapted to pierce the loop of suture 71 loop in a second location. According to the invention, the pierce of the prong cleat 73 can partially engage the thickness of the suture 71 or create a second bifurcation 74 in the suture.

Figure 4B:
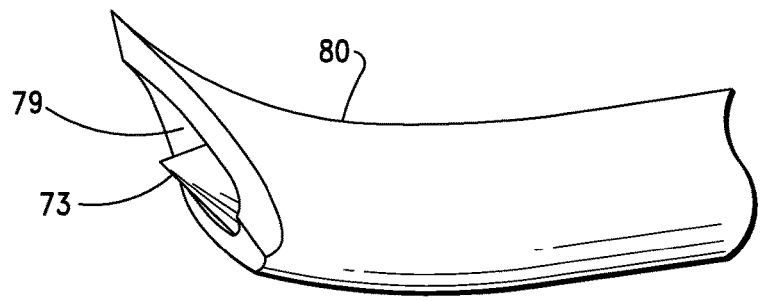
FIG. 4B is a perspective view of the tubular needle shown in FIG. 3A and the cleat member disposed in the lumen thereof, in accordance with the invention.
Figure 4C:
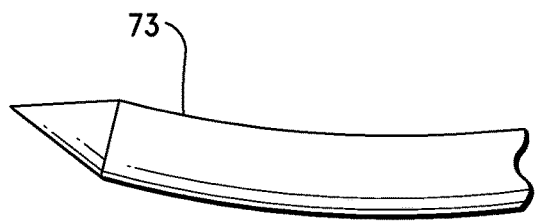
FIG. 4C is a perspective view of the cleat member shown in FIG. 4B, in accordance with the invention.

As illustrated in FIG. 4C, in a preferred embodiment, the prong cleat 73 comprises a wire rod or tube that is housed within the lumen 79 of the tubular needle 70. As further illustrated in FIG. 4C, the prong cleat 73 comprises a sharp distal tip, which slightly extends from the lumen 79 of the tubular needle 70, as illustrated in FIG. 4B. The piercing action of the needle 70 and the prong cleat 73 at different locations in the suture 71 act in conjunction to stabilize the suture 71 and prevent the suture 71 from advancing along the shaft of the needle 70.

Figure 5A:
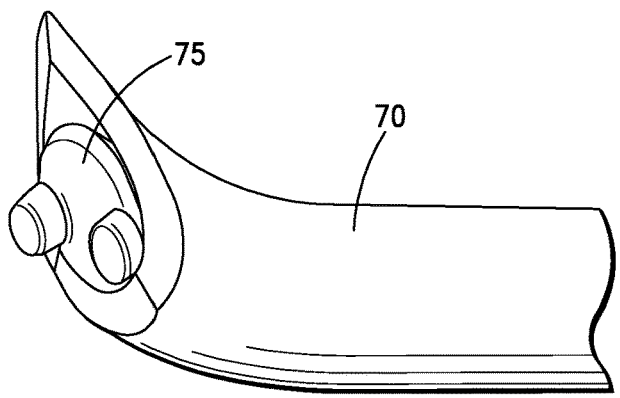
FIG. 5A is a perspective view of the tubular needle shown in FIG. 4B comprising another embodiment of a cleat member disposed in the lumen thereof, in accordance with the invention.
Figure 5B:
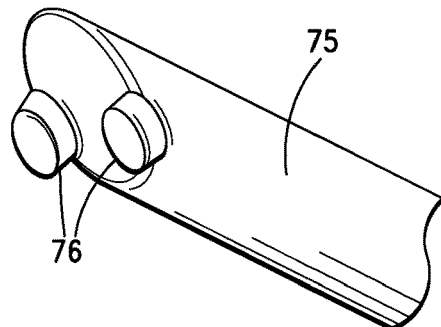
FIG. 5B is a perspective view of the cleat member shown in FIG. 5A, in accordance with the invention.
Figure 5C:
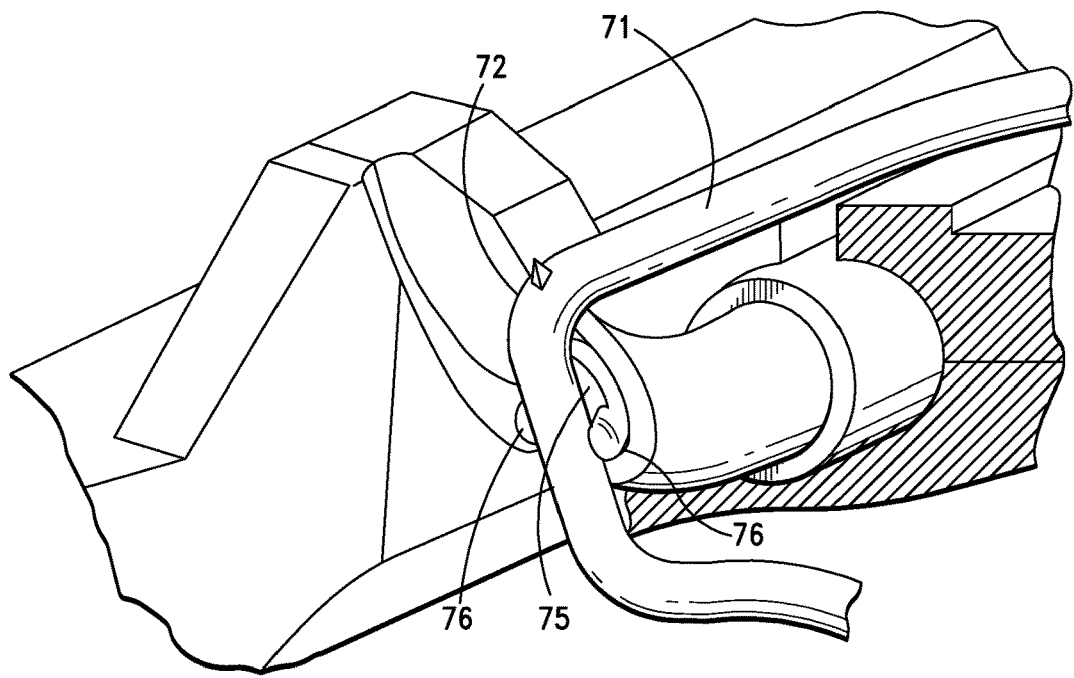
FIG. 5C is a perspective view of the tip, tubular needle, the embodiment of the cleat member shown in FIG. 5A, and suture, in accordance with the invention.

Referring back to FIG. 3C, in another embodiment, tubular needle 70 pierces the loop of suture 71 and creates a bifurcation 72 in the suture 71. When additional force is applied to the suture 71, the bifurcation 72 advances along the shaft of the needle 70. To prevent the bifurcation 72 from advancing along the shaft of the needle 70, a lateral post cleat 75, illustrated in FIG. 5A, is positioned to engage the bifurcated section of the suture 71, as illustrated in FIG. 5C.

Referring now to FIGS. 6A and 6B, there is illustrated a jaw mechanism 40 having an aperture 41 therein, which is sized and configured to receive tubular needle 70 and suture 71 and allow tubular needle 70 and suture 71 to pass through.

As illustrated in FIGS. 6B and 6C, the jaw mechanism further comprises a retractable pawl 42, which includes a window 43 that aligns with aperture 41 when the retractable pawl 42 is extended forward in the open position. When the tubular needle 70 and suture 71 are deployed within aperture 41 via actuator 50, the retractable pawl 42 is then moved to a retracted or rearward position, as illustrated in FIG. 6C. In some embodiments, the retractable pawl actuation mechanism includes a spring bias to provide a relatively constant force of the retractable pawl 42 against the deployed tubular needle 70 and suture 71.

As set forth in Co-pending U.S. application Ser. No. 17/891,328, upon release of the actuator 50, a spring in the actuator mechanism returns the tubular needle 70 to the constraining channel 90. The spring bias of the retractable pawl 42 allows the tubular needle 70 to return yet allows the retractable pawl 42 to maintain a grip on the suture 71 and pulls it in a rearward movement to become captured in between the proximal edge 44 of the aperture 41 in the jaw 40 and distal edge 47 of pawl window 43, as is shown in FIGS. 6C and 6D. Complete release of the actuator 50 disengages the jaw mechanism 40 to the default open position, thus, completing the passage of suture 71 through the tissue.

Figure 7A:
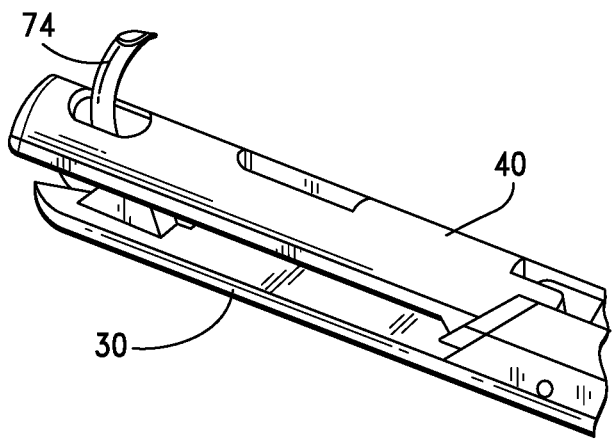
FIG. 7A is a perspective view of another embodiment of a suture passing device comprising two tubular needles and a jaw mechanism with the left tubular needle extended through the aperture of the jaw mechanism, in accordance with the invention.

As further set forth in Co-pending U.S. application Ser. No. 17/891,328, in some embodiments, the suture passing device is configured to comprise two (2) or more tubular needles 70. In one embodiment, the suture passing device can throw more than one segment of suture 71 through tissue simultaneously. An exemplar two needle suture passing device is illustrated in FIG. 7A, which shows a left tubular needle 74 and a right tubular needle (denoted "75", but not illustrated) after being released to their natural states.

The segments of suture being passed by multiple tubular needles 70 can be attached to form a continuous loop of suture, thus enabling the formation of a desired suture pattern, e.g., a horizontal mattress stitch.

In some embodiments of the invention, the suture passing device is configured to deploy the left needle 74 and right needle 75 independently.

Figure 7B:
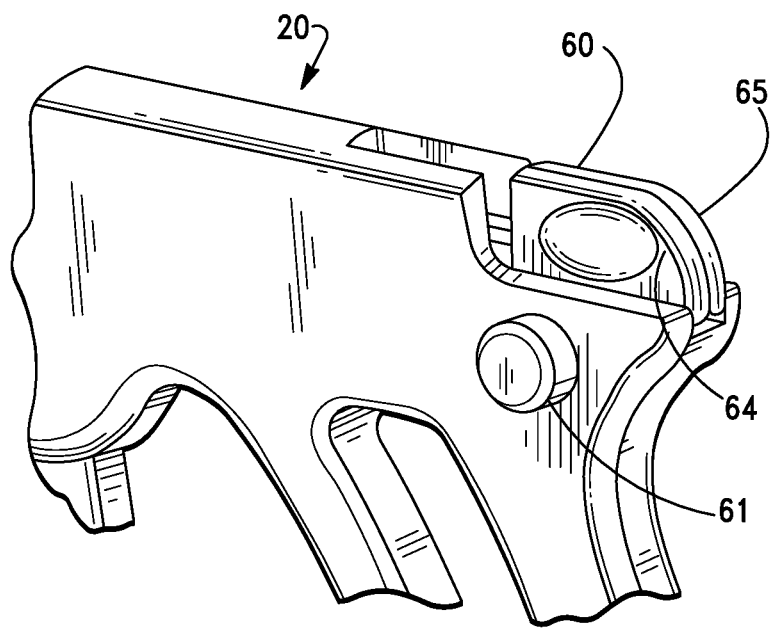
FIG. 7B is a perspective view of the hand grip, toggle switch and needle assemblies of the suture passing device shown in FIG. 7A, in accordance with the invention.

Referring now to FIG. 7B, there is illustrated another embodiment of handle mechanism 20 that is adapted to modulate multiple needles independently. As illustrated in FIG. 7B, the handle mechanism 20 comprises a switch 61 to toggle and engage one needle assembly at a time in the drive track 60. When the switch 61 is toggled to engage the left needle assembly 64, the jaw mechanism 40 can be actuated to grasp a desired location of tissue and the left tubular needle 74 is deployed to pass and capture suture in a first tissue location.

As further set forth in Co-pending U.S. application Ser. No. 17/891,328, fully releasing the actuator 50 returns the left tubular needle 74 to its constrained state and disengages jaw mechanism 40. The suture passing device can then be repositioned to a second desired tissue location. When the switch 61 is toggled to engage the right tubular needle 75, the jaw mechanism 40 can be actuated to grasp a second desired location of tissue and the right needle 75 is deployed to pass and capture suture in a second tissue location. Fully releasing the actuator 50 returns the right tubular needle 75 to its constrained state and disengages jaw mechanism 40 from tissue. The suture passing device can then be removed from the cannula to expose the two ends of the suture.

As further set forth in Co-pending U.S. application Ser. No. 17/891,328 and illustrated in FIGS. 8A-8C, in some embodiments, the suture passing device described above comprises a floating pivot mechanism to facilitate a lower profile when the jaw mechanism 40 and tip 30 are separated. In some embodiments, the jaw mechanism 40 thus includes a pivot interface 36 with a linkage 35. At the opposite end of linkage 35 is another pivot interface 37 that joins linkage 35 and drive rod 38.

Figure 8A:
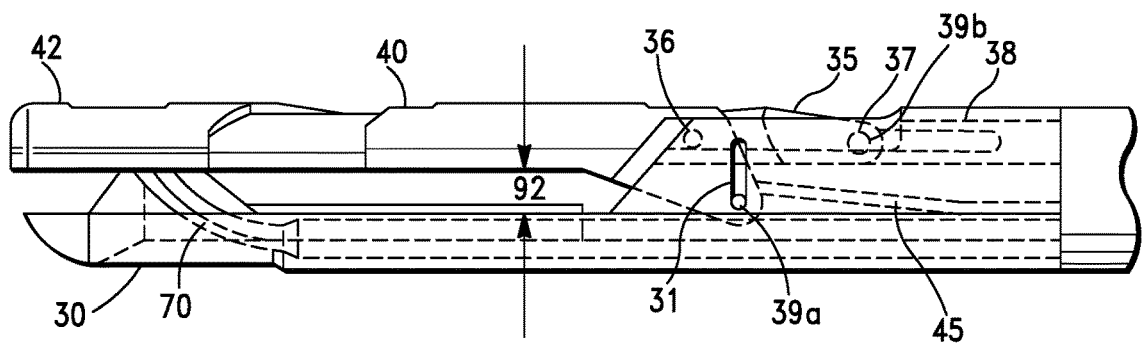
FIG. 8A is a side plan view of the tip shown in FIG. 6A with a slot and floating pivot mechanism in the collapsed state, in accordance with the invention.
Figure 8B:
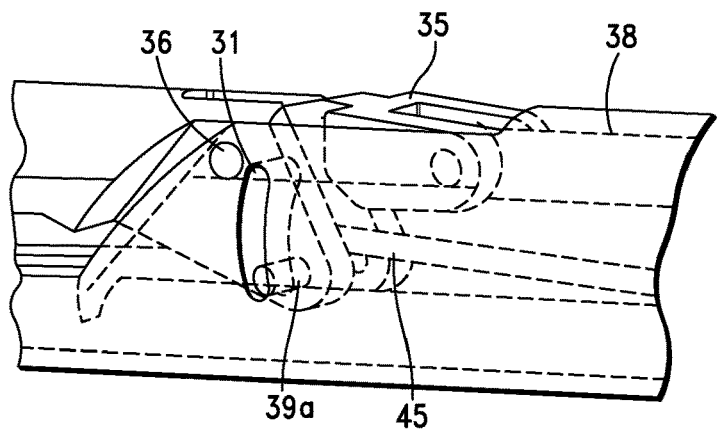
FIG. 8B is a perspective view of the floating pivot mechanism, in accordance with the invention.

As illustrated in FIGS. 8A and 8B, the tip 30 includes a slot 31 in which a pin 39a slidably translates within. The pin 39a is fixed to jaw mechanism 40. Axial movement of drive rod 38 in relation to the tip 30 causes jaw mechanism 40 to rotate about pin 39a in relationship to the tip 30.

As further illustrated in FIGS. 8A and 8B, a leaf spring 45 exerts a force on the pin 39a to bias the pin 39a against the lower end of slot 31, thus, resulting in the jaw mechanism 40 being positioned in a collapsed state and the gap 92 between the inner surfaces of the tip 30 and jaw mechanism 40 being minimized.

The collapsed state of the jaw mechanism 40 is advantageous for providing a minimum profile for advancing the device through an access cannula. According to the invention, the device can be configured to be advanced into the through an access cannula having a diameter in the range of 2.0 mm-15.0 mm, more preferably, in the range of 5.0 mm-8.0 mm.

Figure 8C:
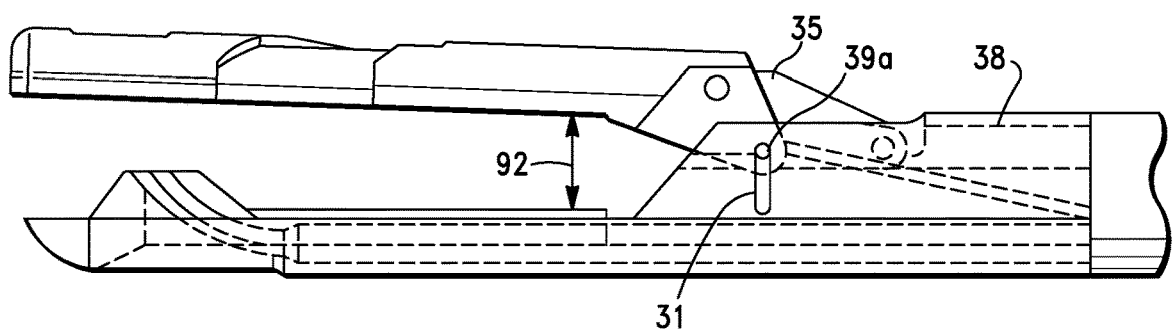
FIG. 8C is a side plan view of the tip shown in FIG. 6A with a slot and floating pivot mechanism in the expanded or vertically articulated state, in accordance with the invention.

When the tip 30 and jaw mechanism 40 are positioned proximate tissue, advancement of the drive rod 38 causes the jaw mechanism 40 to rotate about pin 39a to clamp onto the tissue. The resisting force of the tissue to compression between tip 30 and the jaw mechanism 40 results in a force applied to the inner surface of the jaw mechanism 40. If the force applied to the inner surface of the jaw mechanism 40 exceeds the force of the leaf spring 45 provided to hold the pin 39a against the lower end of slot 31, the pin 39a will ride up the slot 31, and increase the gap 92 between the inner surfaces of tip 30 and the jaw mechanism 40, as illustrated in FIG. 8C.

In some embodiments, the gap 92 between the inner surfaces of tip 30 and the jaw mechanism 40 comprises a width in the range of 0.5 mm-5.0 mm, more preferably, a width in the range of 1.5 mm-3.3 mm.

Figure 9A:
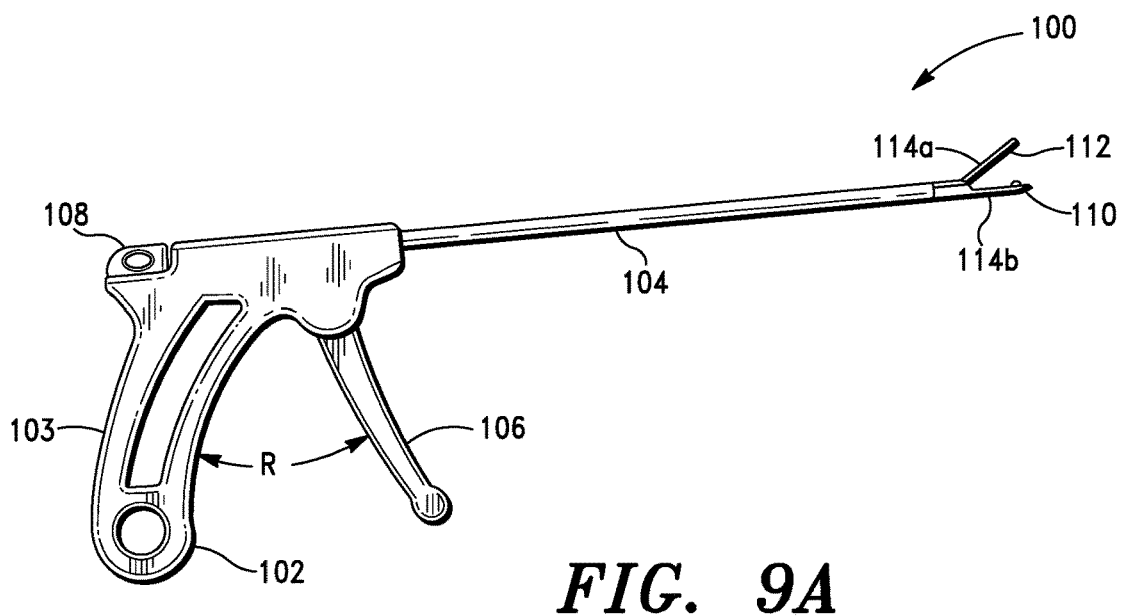
FIGS. 9A-9C are side plan views of another embodiment of a suture passing device in various stages of deployment, in accordance with the invention.
Figure 9B:
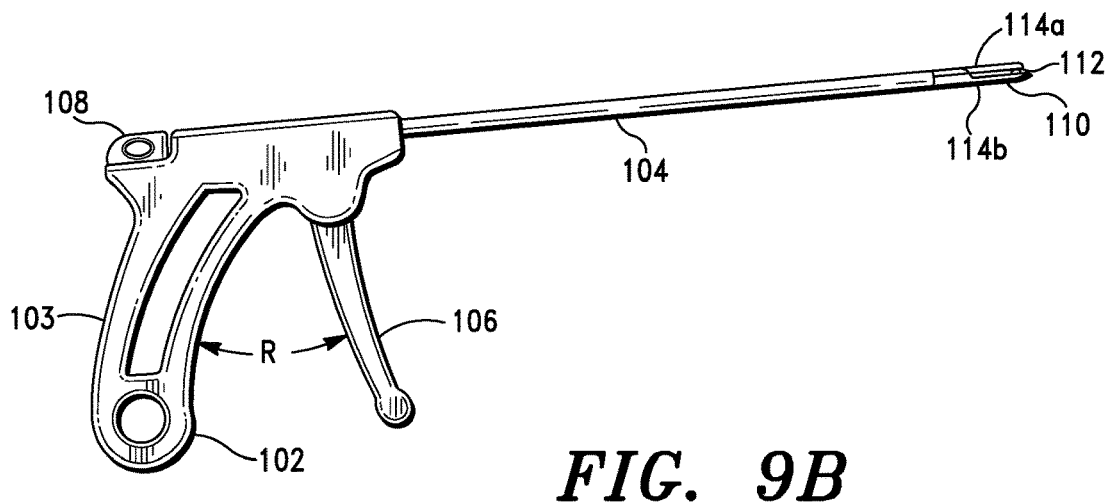
Figure 9C:
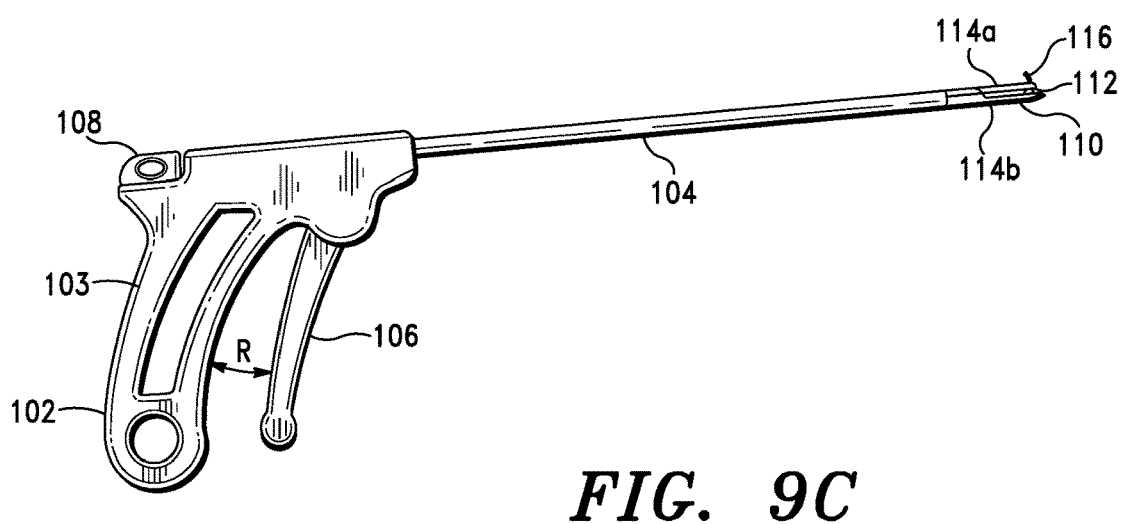

Referring now to FIGS. 9A-9C, there is shown another embodiment of a suture passing device 100 at various stages of actuation. As illustrated in FIG. 9A, the suture passing device 100 of the present invention comprises a hand grip 102 in operative communication with elongated tubular body or member 104 having a distal end 110.

As further illustrated in FIG. 9A, hand grip 102 comprises a proximal end 103, an actuator 106 and a needle assembly 108, and elongated tubular member 104 comprises a jaw mechanism 112 having top and bottom members 114a, 114b disposed proximate the elongated tubular member 104 distal end 110. In a preferred embodiment, the jaw mechanism 112 top and bottom members 114a, 114b comprise proximal and distal ends.

In a preferred embodiment, the jaw mechanism 112 of the suture passing device 100 similarly comprises the floating pivot mechanism and pivot interface discussed above and shown in FIGS. 8A-8C to facilitate a lower profile when the top and bottom members 114a, 114b of jaw mechanism 112 are separated and during axial articulation of the top and bottom members 114a, 114b.

In the noted embodiments, the jaw mechanism 112 preferably comprises first and second pins 39a, 39b, the proximal end of the jaw mechanism 112 top member 114a comprises first and second pin lumens, and the proximal end of the jaw mechanism 112 bottom member 114b comprises a third pin lumen and a pin slot 31.

Preferably, the first pin lumen and the pin slot 31, and the second and third pin lumens are in axial alignment.

In a preferred embodiment, the jaw mechanism 112 top member 114a first pin lumen and the bottom member 114b pin slot 31 are configured to receive and position the jaw mechanism 112 first pin 39a, wherein, when the jaw mechanism 112 first pin 39a is received by and positioned in the jaw mechanism 112 top member 114a first pin lumen and the bottom member pin slot 31, the jaw mechanism 112 top member 114a is allowed to vertically or linearly articulate with respect to the jaw mechanism 112 bottom member 114b.

In a preferred embodiment, the jaw mechanism 112 top member 114a second pin lumen and the bottom member 114b third pin lumen are configured to receive and position the jaw mechanism 112 second pin 39b, wherein, when the jaw mechanism 112 second pin 39b is received by and positioned in the jaw mechanism 112 top member 114a second pin lumen and the bottom member third pin lumen, the jaw mechanism 112 top member 114a is allowed to axially or rotatably articulate with respect to the jaw mechanism 112 bottom member 114b.

According to the invention, any of the embodiments of the jaw mechanisms described herein can comprise the floating pivot mechanism and pivot interface discussed above and shown in FIGS. 8A-8C.

According to the invention, the suture passing device 100 can be used to capture and maintain biological tissue by positioning the jaw mechanism 112 of the suture passing device 100 proximate the tissue applying a first radial force on the actuator 106 to transition the top and bottom members 114a, 114b of jaw mechanism 112 from an open configuration, as illustrated in FIG. 9A, to a closed configuration, as illustrated in FIG. 9B. A second radial force can also be applied to actuator 106 to deploy a tubular needle 116 having a suture attached thereto into and through the tissue, as illustrated in FIG. 9C and discussed in detail below.

In a preferred embodiment, the actuator 106 provides axial articulation of top member 114a relative to bottom member 114b of jaw mechanism 112. In some embodiments, the actuator 106 can be coupled to a return spring (not shown) that biases the actuator 106 in the open configuration shown in FIG. 9A.

In some embodiments of the invention, the actuator 106 of the hand grip 102 comprises a spring-loaded mechanism that is configured to provide a resistance force on the actuator 106 to provide tactile feedback for the operator to indicate that the tubular needle 116 is slidably translating into and through the jaw mechanism 112.

Figure 10A:
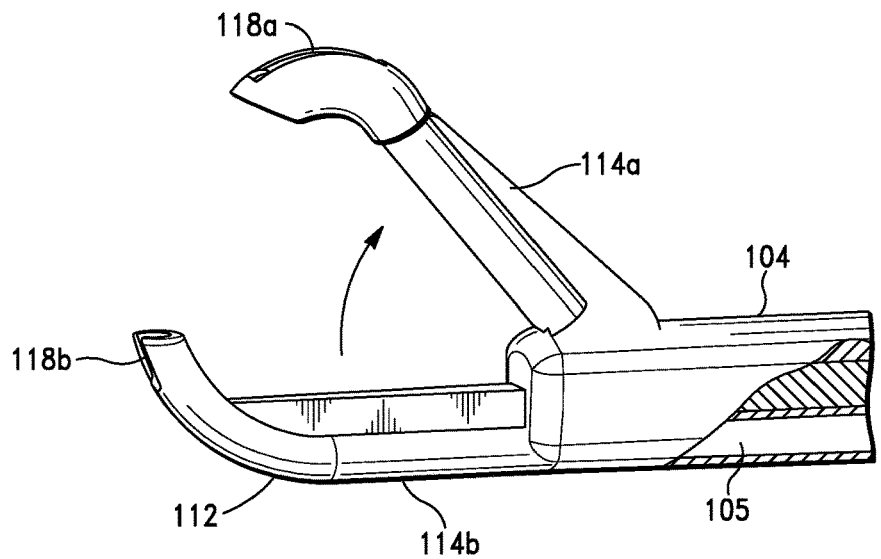
FIG. 10A is a side plan partial sectional view of an elongated member distal tip and jaw mechanism of the suture passing device shown in FIG. 9A prior to loading a suture, in accordance with the invention.

Referring now to FIG. 10A, there are shown top and bottom members 114a, 114b of jaw mechanism 112 in an open configuration. As illustrated in FIG. 10A, the top member 114a comprises a guide channel 118a and the bottom member 114b comprises a guide channel 118b. In a preferred embodiment, the guide channels 118a, 118b are sized and configured to receive tubular needle 116 of the invention therein.

As further illustrated in FIG. 10A, in a preferred embodiment, guide channel 118b is in aligned communication with the elongated member 104 internal lumen 105.

Figure 10B:
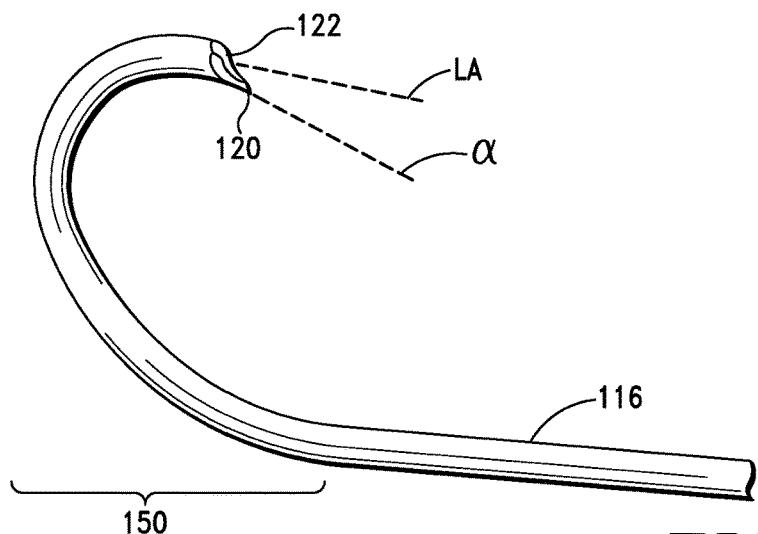
FIG. 10B is a side plan view of a preformed tubular needle, in accordance with the invention.
Figure 11A:
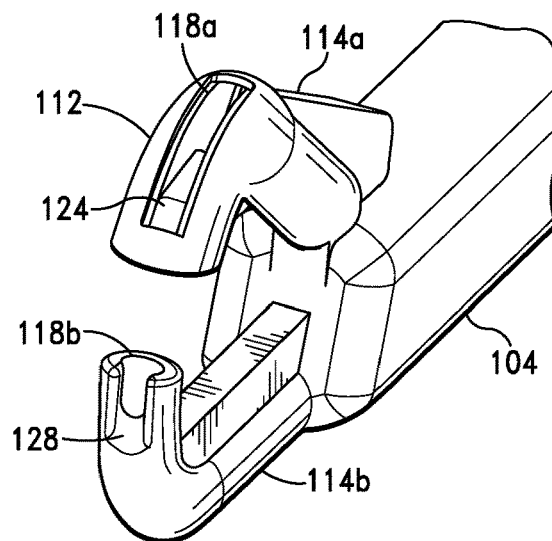
FIG. 11A is a perspective view of the elongated member distal tip and jaw mechanism of the suture passing device shown in FIG. 10A showing the pawl feature, in accordance with the invention.
Figure 11B:
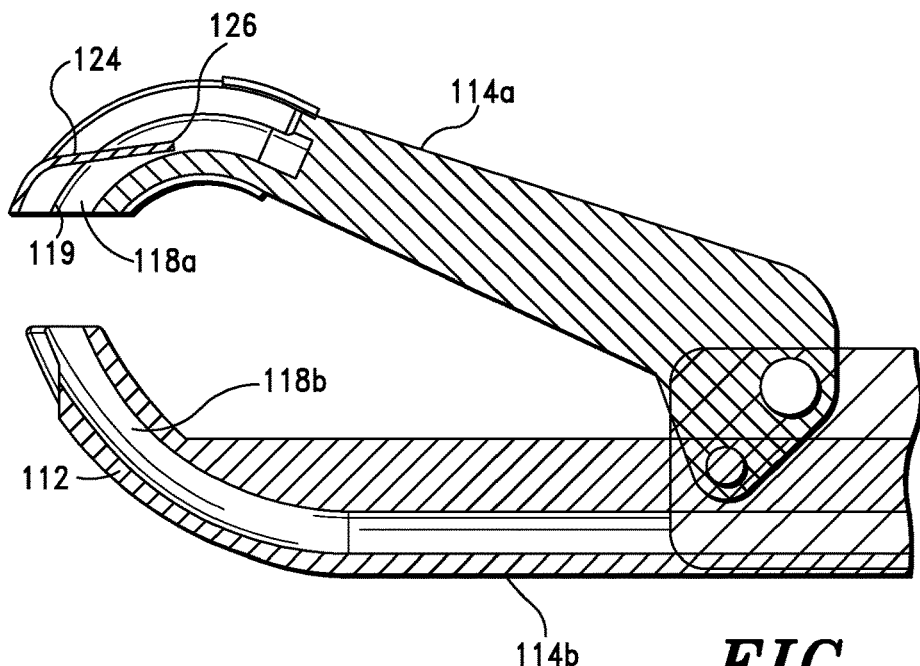
FIG. 11B is a side plan sectional view of the elongated member distal tip and jaw mechanism shown in FIG. 10A showing the track for the needle, in accordance with the invention.
Figure 11C:
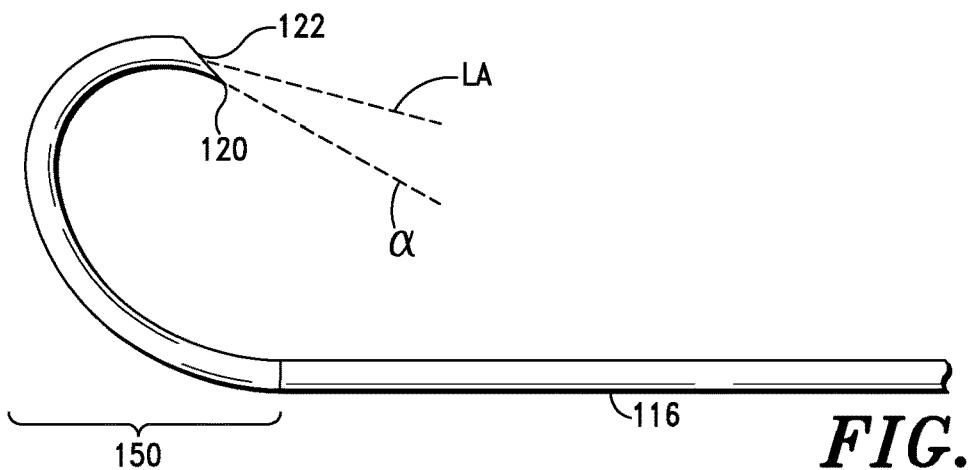
FIG. 11C is another side view of the tubular needle shown in FIG. 10B comprising two segments to match a guide channel track profile, in accordance with the invention.

Referring now to FIGS. 10B and 11C, there is shown tubular needle 116 in a first natural state comprising a distal end 120 and internal lumen 122. As illustrated in FIG. 10B, the tubular needle 116 comprises a formed curvilinear portion 150.

In some embodiments, the tubular needle 116 comprises multiple curvilinear sections 150 to slidably translate into and through the guide channels 118a, 118b. According to the invention, the curvilinear portion 150 of the tubular needle can comprise any suitable shape where 6.0% strain is not exceeded.

In a preferred embodiment, the tubular needle 116 comprises nickel-titanium alloy (Nitinol®) and is configured to transition (or deform) from an unconstrained or natural state to a constrained state, and from the constrained state back to the unconstrained state. As illustrated in FIG. 10B, in a preferred embodiment, the unconstrained state tubular member 116 comprises formed curvilinear portion 150.

Figure 10C:
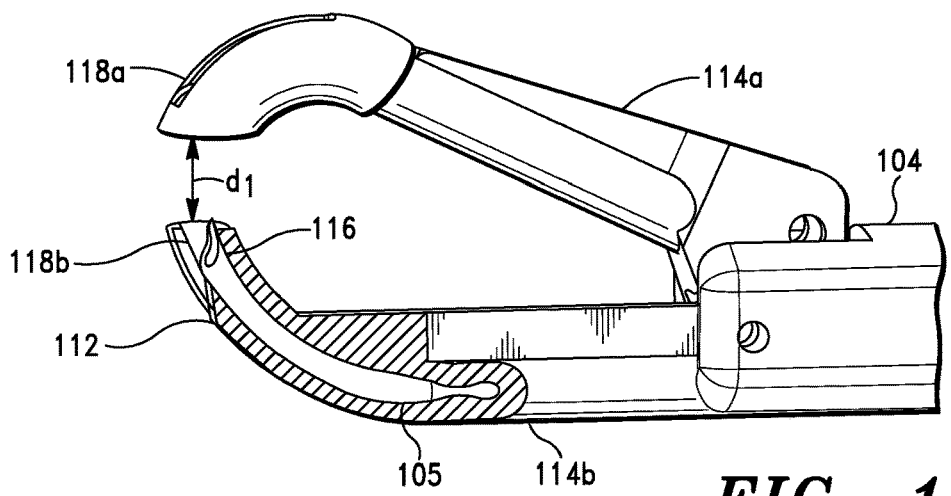
FIG. 10C is a side plan partial sectional view of a preformed tubular needle retracted and constrained in the guide channel of the bottom jaw member, and the jaw mechanism set at a determined gap distance, in accordance with the invention.

As shown in FIG. 10C, in some embodiments, the tubular needle 116 is adapted to transition or deform into a constrained state when the curvilinear portion 150 of the tubular needle 116 is advanced through the elongated tubular member 104 internal lumen 105 and into guide channel 118b of the jaw mechanism 112 bottom member 114b.

In some embodiments, the curvilinear portion 150 of the tubular needle 116 is adapted to reassume a curvilinear shape upon further advancement out of guide channel 118b and into and through guide channel 118a of the jaw mechanism 112 top member 114a.

In some embodiments, the tubular needle 116 comprises a hollow and rigid structure. In some embodiments, the tubular needle 116 comprises geometry where the area moment of inertia about the neutral bending axis is in the range of $20.0 \times 10^{-9}$-$300.0 \times 10^{-9}$ inches to the $4^{th}$ power, more preferably, the tubular needle comprises a geometry where the area moment of inertia about the neutral bending axis in the range of $25.0 \times 10^{-9}$-$75.0 \times 10^{-9}$ inches to the $4^{th}$ power, which allows the tubular needle 116 to be driven into biological tissue with minimal deflection or skiving.

According to the invention, the tubular needle 116 distal end 120 can comprise various configurations, including, but not limited to, a beveled, curved, and serrated edge, which is configured to pierce through biological tissue.

In a preferred embodiment, the tubular needle 116 distal end 120 comprises a beveled edge having an angle "α" in the range of approximately 1°-90° with respect to the longitudinal axis "LA" of the tubular needle 116. More preferably, the angle "α" of the beveled distal end 120 is in the range of approximately 45°-90°.

In some embodiments, the needle 116 comprises a solid structure.

Referring now to FIG. 10C, there are shown top and bottom members 114a, 114b of jaw mechanism 112 in a closed configuration comprising tubular needle 116 disposed in the guide channel 118b of bottom member 114b. As illustrated in FIG. 10C, the top and bottom members 114a, 114b of jaw mechanism 112 comprise a reciprocating curvilinear configuration that is configured to align guide channels 118a, 118b and, thereby, approximate the same curvilinear shape or configuration as the formed curvilinear portion 150 of the tubular needle 116 when the jaw mechanism 112 is in a closed configuration.

As further illustrated in FIG. 10C, when the top and bottom members 114a, 114b of jaw mechanism 112 are in a closed configuration the top and bottom members 114a, 114b are configured to be partially closed at a set distance di from each other.

In some embodiments, the top and bottom members 114a, 114b are configured to fully close to facilitate passage through an access cannula.

In a preferred embodiment, the needle assembly 108 and the tubular needle 116 in communication therewith are engaged to the proximal end 103 of hand grip 102 and the tubular needle 116 is slidably transitioned into and through the elongated tubular member 104 internal lumen 105 in a constrained state.

Referring now to FIGS. 11A and 11B, there is illustrated pawl 124 of the top member 114a of jaw mechanism 112. As illustrated in FIGS. 11A and 11B, the pawl 124 comprises a distal end 126 and intersects the guide channel 118a and, hence, the path defined by the guide channel 118a.

Figure 12A:
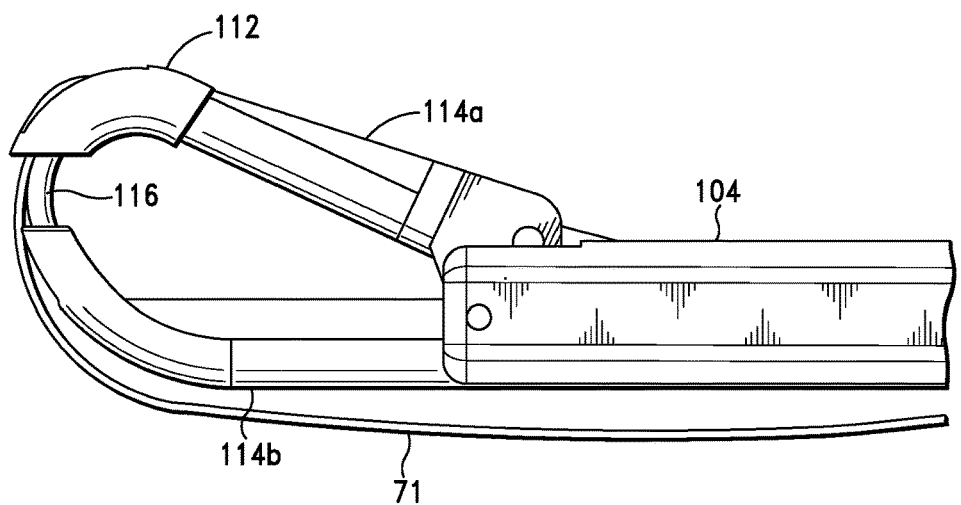
FIG. 12A is a perspective view of the suture passing device shown in FIG. 10A showing the elongated member distal tip, jaw mechanism, and tubular needle extended with suture, in accordance with the invention.
Figure 12B:
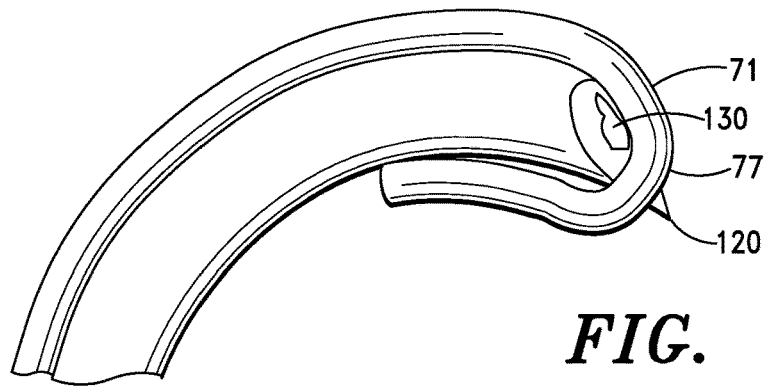
FIG. 12B is a perspective view of the tubular needle and cleat member shown in FIG. 10A extended to engage and carry the suture through the aperture of the jaw mechanism, and pawl, in accordance with the invention.

As further illustrated in FIG. 11A, the bottom member 114b of jaw mechanism 112 comprises a capture lip 128 that is configured to facilitate the capture of a portion of suture 71 shown in FIG. 12B.

Figure 12C:
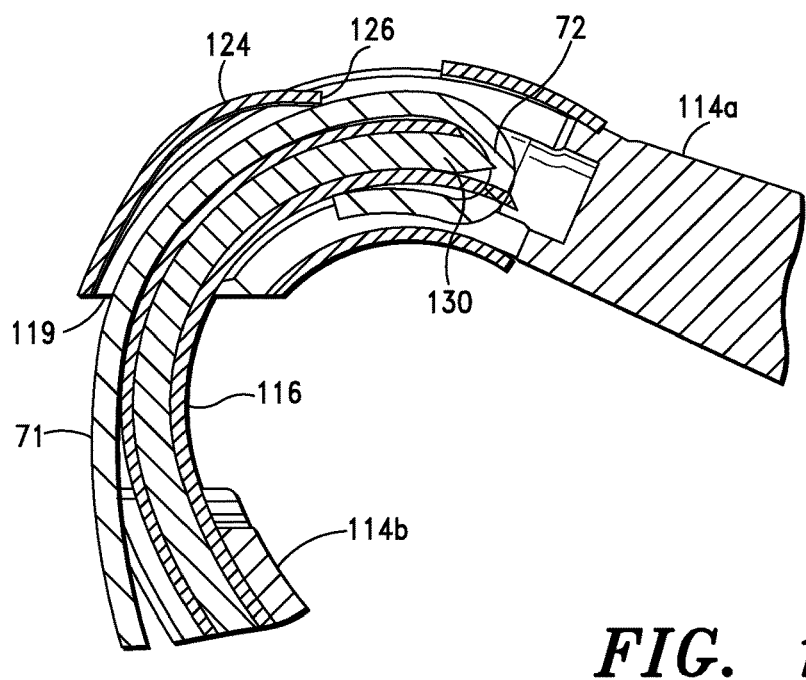
FIG. 12C is a side plan sectional view of the elongated member distal tip, jaw mechanism, tubular needle and cleat member shown in FIG. 10A, and the suture loaded on the distal end of the tubular needle, in accordance with the invention.

As further set forth in Co-pending U.S. application Ser. No. 17/891,328, in some embodiments, the pawl 124 is used as a suture capturing mechanism. Referring now to FIG. 12C, when the tubular needle 116 guides the suture 71 into the guide channel 118a the pawl 124 is deflected, which allows the suture 71 to be guided beyond the distal end 126 of the pawl 124 by tubular needle 116.

According to the invention, when the tubular needle 116 is retracted from the guide channel 118a past the pawl 124, the distal end 126 of pawl 124 exerts a closure force on the suture 71 and captures the suture 71 between the pawl 124 distal end 126 and the inner wall 119 of guide channel 118a.

Referring now to FIGS. 12B and 12C, there is shown suture 71 having a distal end 77 that is loaded onto the distal end 120 of the tubular needle 116. As illustrated in FIGS. 12B and 12C, the distal end 120 of tubular needle 116 is configured to pierce at least a portion of suture 71.

As further illustrated in FIG. 12B, in a preferred embodiment, the distal tip 120 of tubular needle 116 is configured to pierce and form a bifurcation 72 in the suture 71.

As illustrated in FIGS. 12B and 12C, in some embodiments, the tubular needle 116 comprises a cleat member 130 having a piercing distal end 132 and is positioned in the tubular needle 116 internal lumen 122 and configured to pierce and engage at least a portion of the suture 71.

In a preferred embodiment, the tubular needle 116 distal end 120 and the cleat member 130 distal end 132 are adapted to pierce and engage suture 71 at two (2) predetermined locations on the suture 71 to secure the suture 71 thereto.

Figure 13A:
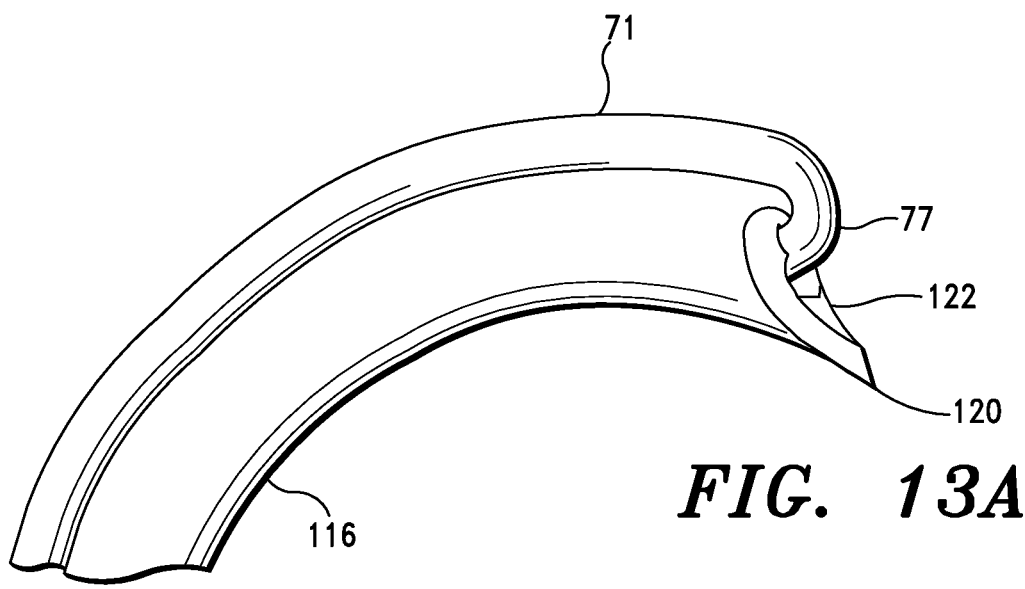
FIG. 13A is a perspective view of the tubular needle of the suture passing device shown in FIG. 10A with a front-loaded suture, in accordance with the invention.
Figure 13B:
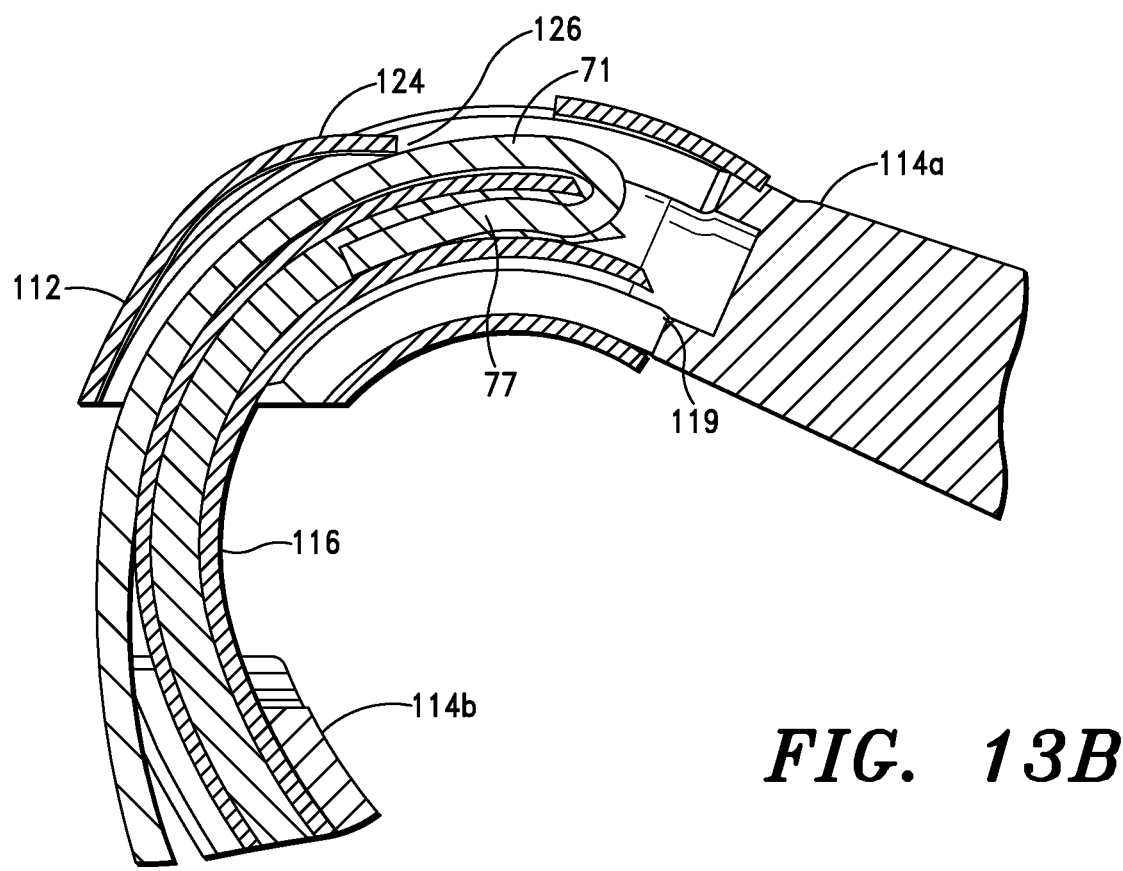
FIG. 13B is a side plan sectional view of the elongated member distal tip, jaw mechanism, and tubular needle shown in FIG. 10A with a front-loaded suture, in accordance with the invention.

Referring now to FIGS. 13A and 13B, there is illustrated distal end 77 of suture 71 front loaded into the internal lumen 122 of the tubular needle 116 distal end 120. As illustrated in FIGS. 13A and 13B, the bend in the distal end 77 of the suture 71 provides a strain relief section that functions to releasably secure the distal end 77 of the suture 71 to the tubular needle 116 distal end 120 for penetration and advancement into biological tissue. According to the invention, when the tubular needle 116 is retracted from biological tissue, at least a portion of suture 71 is captured and retained by the biological tissue.

As illustrated in FIG. 13B, in some embodiments, the suture 71 distal end 77 is engaged by the distal end 126 of pawl 124, wherein the suture 71 distal end 77 is captured between the distal end 126 of pawl 124 and the inner wall 119 of the guide channel 118a.

Referring now to FIGS. 14-19, there is shown another embodiment of a jaw mechanism (now denoted "212") comprising top and bottom members 214a, 214b and a suture retriever component (or needle shield) 250 that is secured to the jaw mechanism 212 top member 214a.

Figure 14:
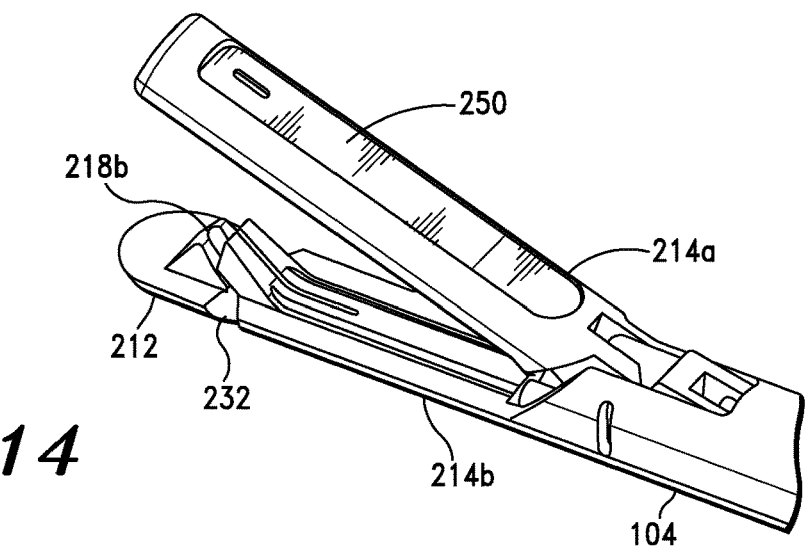
FIG. 14 is a perspective view of another embodiment of the suture passing device comprising a jaw mechanism in the open position with the tubular needle fully retracted, showing the needle shield secured to the jaw mechanism top member, in accordance with the invention.
Figure 15:
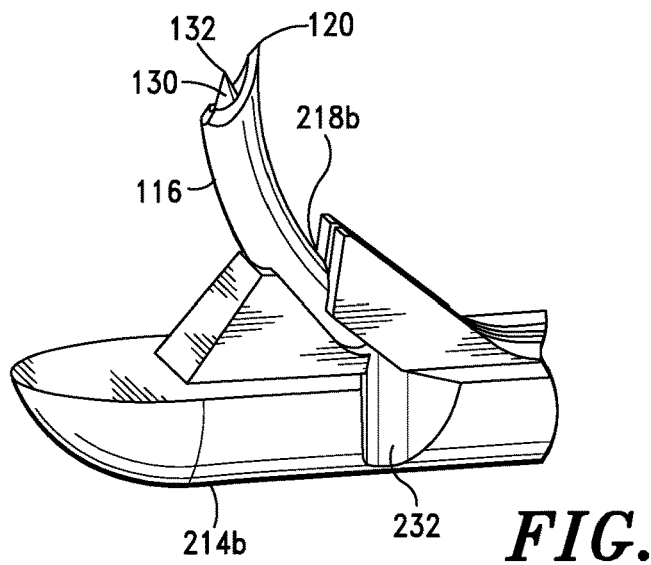
FIG. 15 is a perspective view of tubular needle of the suture passing device shown in FIG. 14 that is extending from the guide channel of the bottom jaw member and transitioning to an unconstrained configuration, in accordance with the invention.
Figure 16:
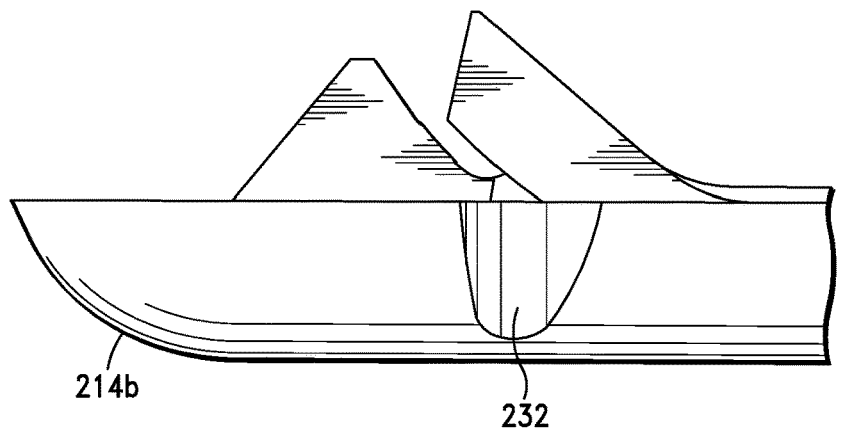
FIG. 16 is a side plan view of the jaw mechanism bottom member shown in FIG. 14 showing the suture loading slot that is disposed on a lateral side of the bottom member, in accordance with the invention.

As illustrated in FIGS. 14-16, the jaw mechanism 212 bottom member 214b similarly comprises a guide channel 218b that is configured to receive tubular needle 116 having cleat member 130 disposed in the internal lumen 122 thereof. As further illustrated in FIGS. 14-16, in a preferred embodiment, the guide channel 218b comprises a curvilinear shape or geometry that is configured to approximate the same curvilinear shape or configuration as the formed curvilinear portion 150 of the tubular needle 116.

In a preferred embodiment, guide channel 218b is in aligned communication with the elongated member 104 internal lumen 105.

As illustrated in FIG. 16, the jaw mechanism 212 bottom member 214b comprises a suture loading slot 232 that transects the guide channel 218b of the bottom member 214b.

Figure 17:
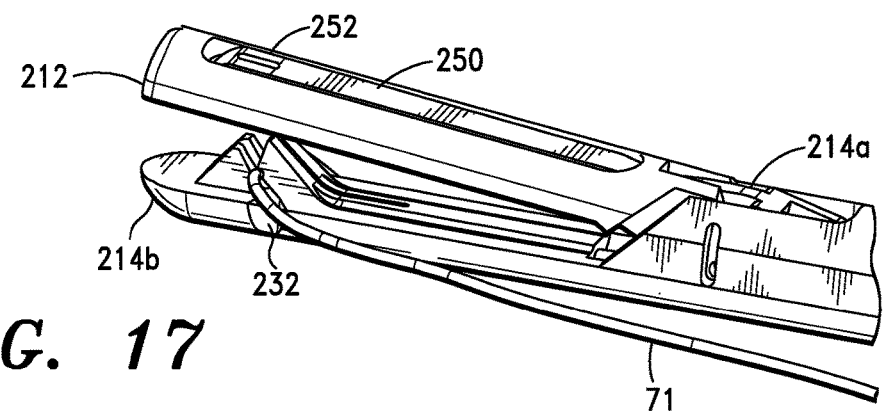
FIG. 17 is a perspective view of the jaw mechanism shown in FIG. 14 with the suture laterally loaded in the jaw mechanism bottom member, in accordance with the invention.

As illustrated in FIG. 17, in a preferred embodiment, the suture 71 is loaded into the suture loading slot 232 from either lateral side, whereby the suture 71 is allowed to slidably translate therethrough and intersect a path defined by the guide channel 218b, wherein the suture 71 can be engaged by the tubular needle 116 as it is slidably translated through guide channel 218b.

Figure 18:
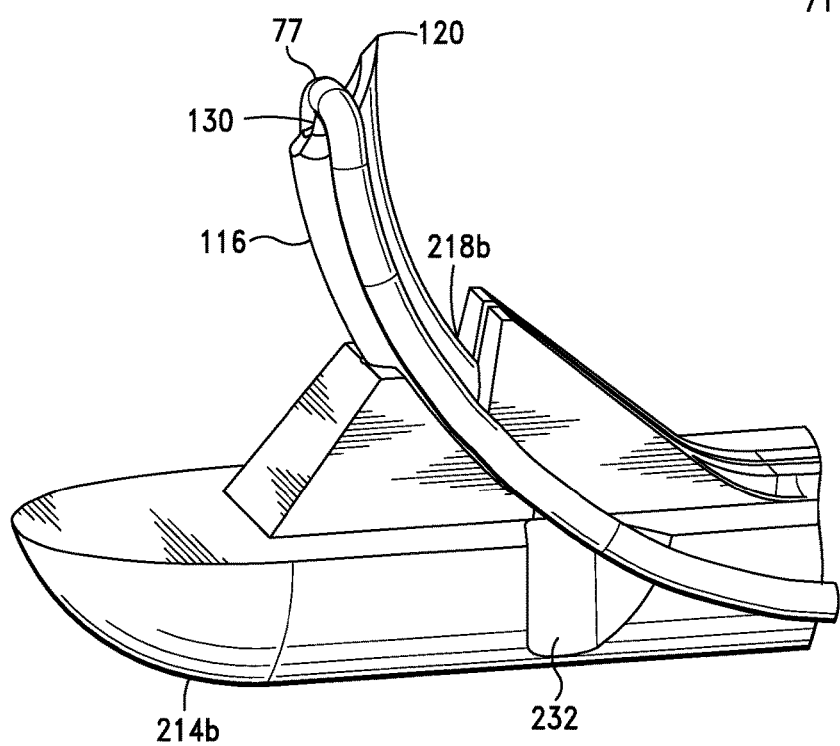
FIG. 18 is a perspective view of a tubular needle of the suture passing device shown in FIG. 14 extended from the guide channel of the bottom jaw member and transitioned to an unconstrained configuration with a suture engaged thereto, in accordance with the invention.
Figure 19:
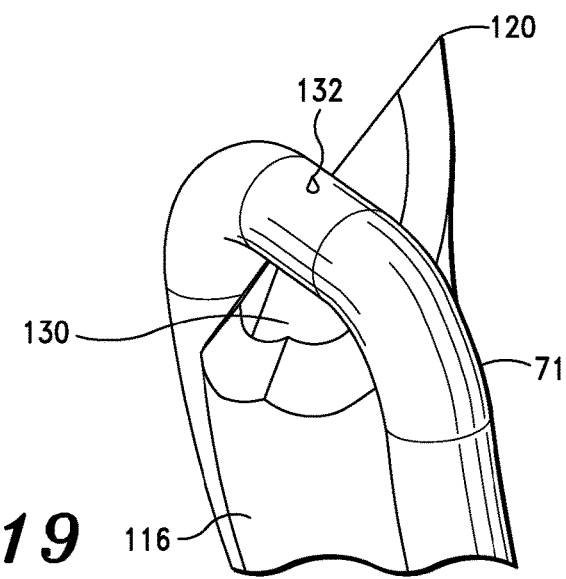
FIG. 19 is a perspective view of the tubular needle shown in FIG. 18 with the cleat member engaged with the suture, in accordance with the invention.

As illustrated in FIGS. 18 and 19, in a preferred embodiment, when the tubular needle 116 comprising cleat member 130 disposed therein is slidably translated through guide channel 218b, the cleat member 130 distal end 132 pierces and engages at least a portion of suture 71. As the tubular needle 116 is slidably translated further through the guide channel 218b of jaw mechanism 212 bottom member 214b, the tubular needle 116 drives the portion of suture 71 forward and into the window 254 of the jaw 212 mechanism top member 214a.

As further illustrated in FIG. 18, in a preferred embodiment, the curvilinear portion 150 of the tubular needle 116 is adapted to transition from a constrained state to an unconstrained state and reassume a curvilinear shape upon further advancement out of guide channel 218b.

Figure 20:
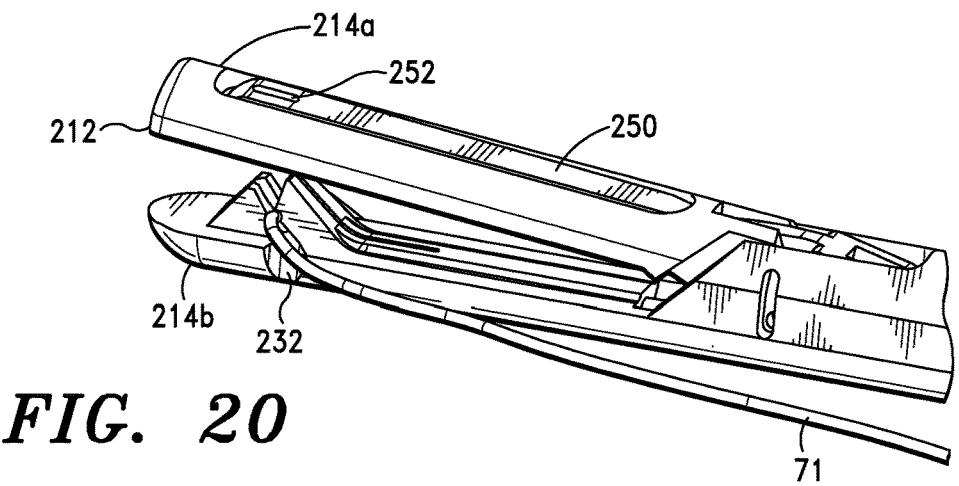
FIG. 20 is a perspective view of the elongated member distal tip and jaw mechanism of the suture passing device shown in FIG. 14, with the tubular needle shield in the default state, in accordance with the invention.
Figure 21:
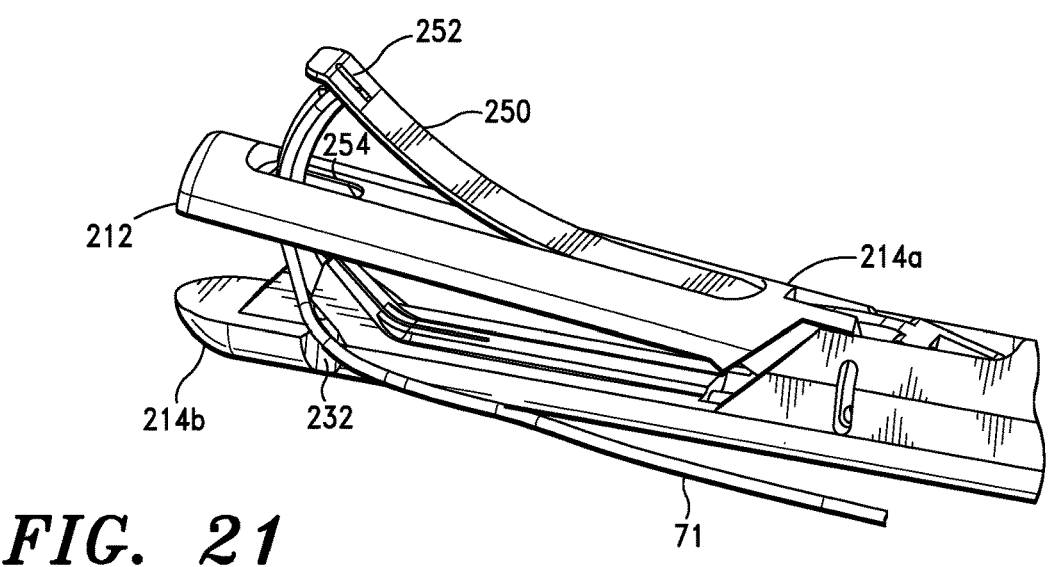
FIG. 21 is a perspective view of the jaw mechanism shown in FIG. 20 with the tubular needle shield in the deflected state, thereby, shielding the tubular needle distal end from surrounding tissue in a surgical site, in accordance with the invention.
Figure 22:
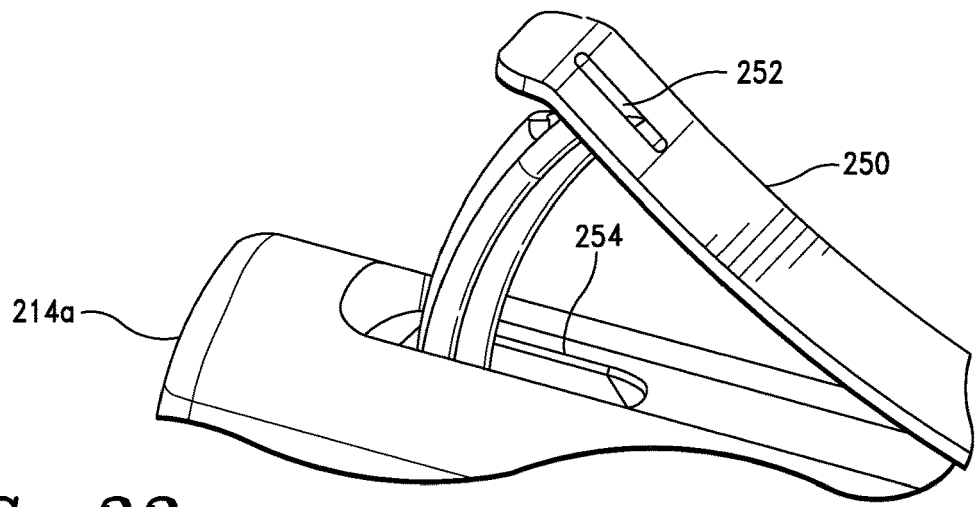
FIG. 22 is a perspective view of the jaw mechanism shown in FIG. 20 with the needle shield in the deflected state, showing a window feature in the needle shield to prevent damage to the tubular needle distal end when the needle is extended into the needle shield, in accordance with the invention.

Referring now to FIGS. 20-22, when the tubular needle 116 is slidably translated through the guide channel 218b and into the window 254 of the jaw mechanism 212 top member 214a, the tubular needle 116 is guided into needle shield 250. As illustrated in FIG. 20, in a preferred embodiment, the needle shield 250 comprises a deflecting trapdoor mechanism that is configured to prevent the tubular needle 116 from penetrating biological tissue and bone beyond the top member 214a and damaging the biological tissue and bone. In a preferred embodiment, the needle shield 250 is configured to deflect and flex when the tubular needle 116 distal end 120 is slidably translated into the needle shield 250.

In a preferred embodiment, the needle shield 250 of the jaw mechanism 212 top member 214a enables antegrade and retrograde passing of suture 71 during an endoscopic procedure, which allows an operator to generate a wide variety of stitch patterns including, without limitation, modified Mason-Allen, mattress, sliding mattress, Mason-Allen, farnear-near-far, Bunnell-Mayer, three-loop pulley, locking loop, modified Kessler, simple interrupted, simple continuous, Ford interlocking, interrupted cruciate, interrupted horizontal mattress, continuous horizontal mattress, interrupted vertical mattress, quilled, interrupted or continuous Lembert, interrupted quilt, Cushing, Connel, Parker-Kerr, purse string and modified variants thereof.

In some embodiments, the needle shield 250 is configured to provide a closure force that captures the suture 71 when the tubular needle 116 is retracted and the needle shield 250 is relieved from the force applied to the needle shield 250 by slidable translation of the tubular needle 116.

As illustrated in FIGS. 20-22, in a preferred embodiment, the needle shield 250 comprises a window member 252 that is configured to protect the distal end 120 of tubular needle 116 from damage. According to the invention, the needle shield 250 can comprise other features to protect the distal end 120 of tubular needle 116, such as a coined recess or other geometry that is configured to receive the distal end 120 of tubular needle 116 without damaging the distal end 120.

According to the invention, the window member 252 can comprise any shape or size suitable to receive the distal end 120 of tubular needle 116 without damaging the distal end 120.

Referring now to FIGS. 23-28B, there is shown another embodiment of a suture passing device of the invention (denoted "400").

Figure 23:
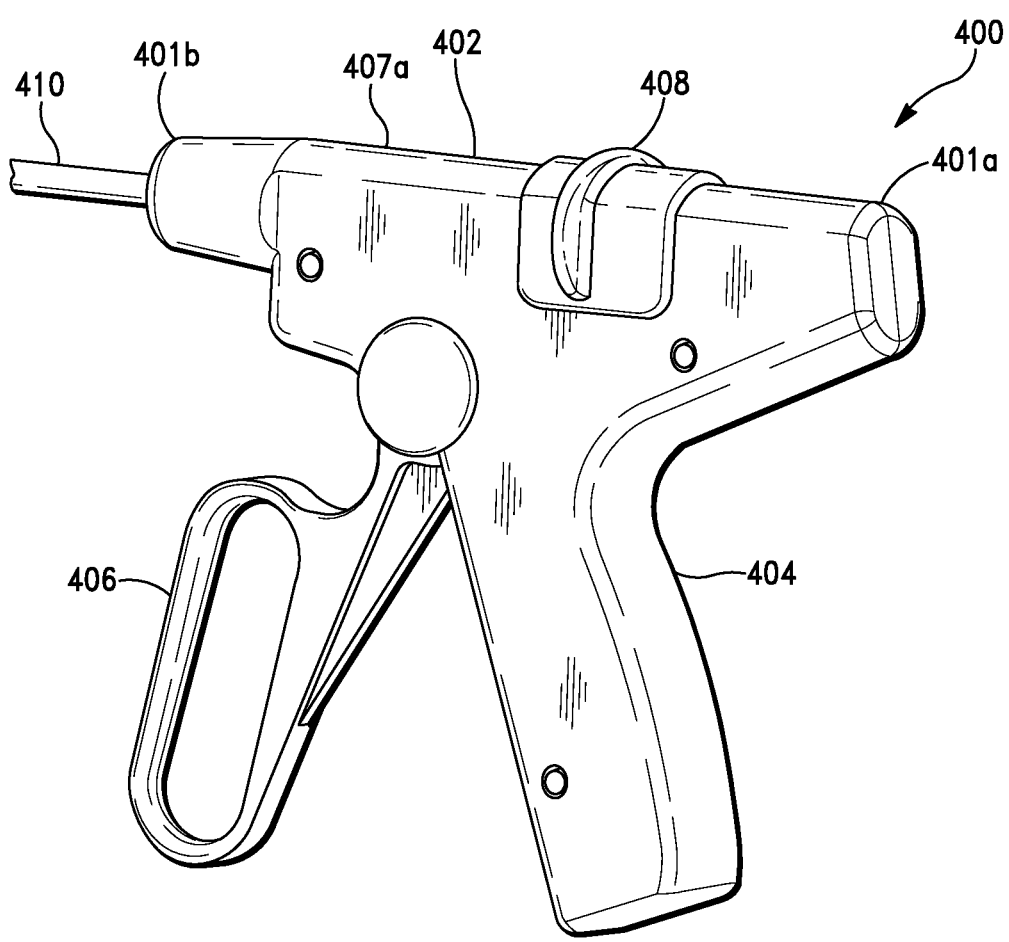
FIG. 23 is a perspective view of another embodiment of the suture passing device, in accordance with the invention.

As illustrated in FIGS. 23 and 24A, the suture passing device 400 similarly comprises a body 402, comprising proximal and distal ends 401a, 401b, a handle 404, a trigger 406, and an elongated member or shaft 410 that similarly comprises a jaw mechanism (denoted "460" in this embodiment), which is adapted to grasp biological tissue.

Figure 24C:
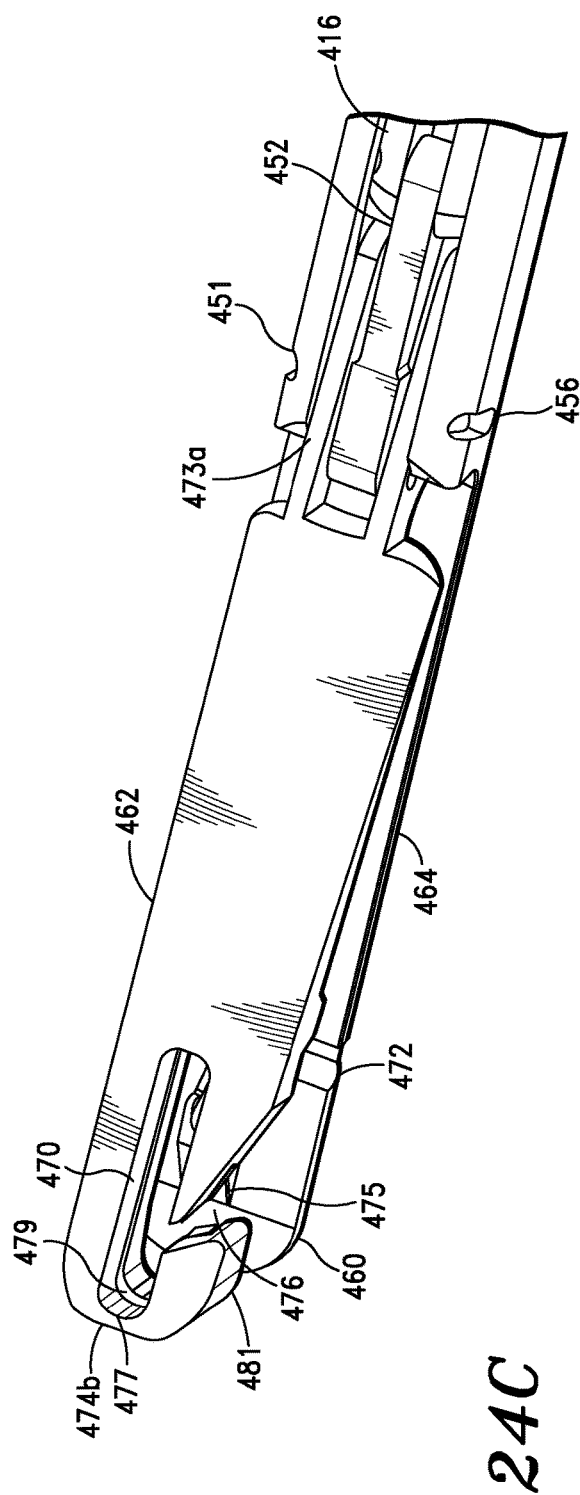
FIG. 24C is a top plan view of the jaw mechanism shown in FIG. 24A, in accordance with the invention.
Figure 24D:
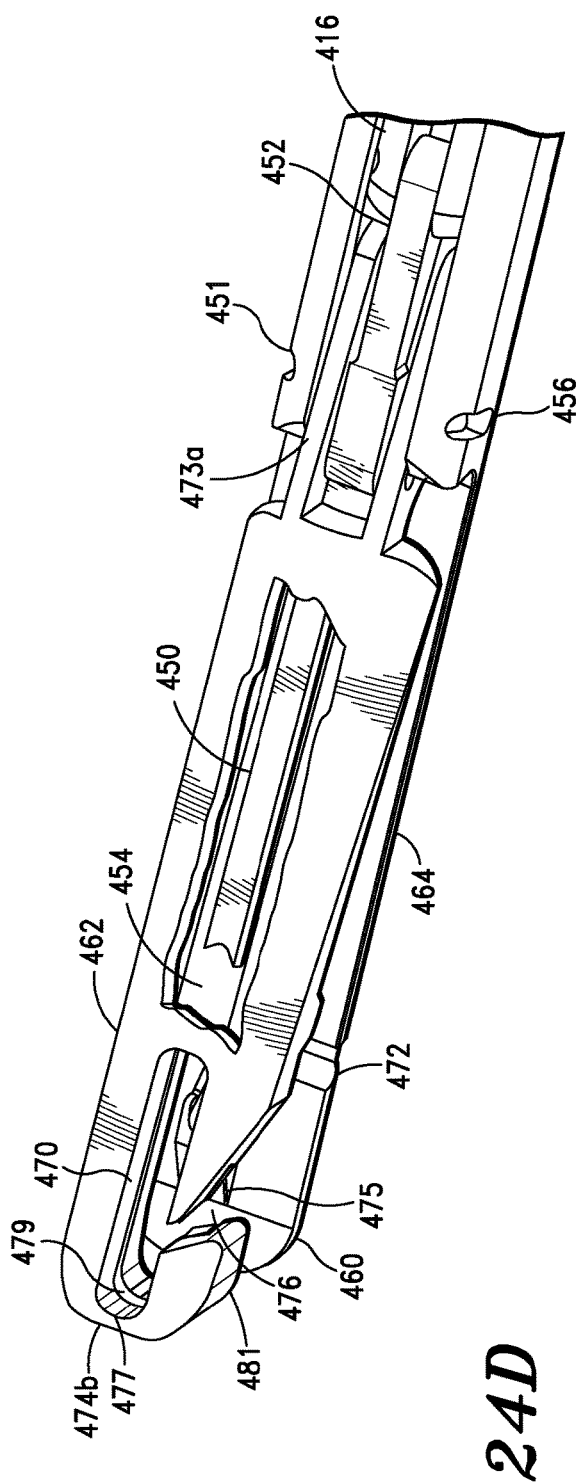
FIG. 24D is a further top plan view of the jaw mechanism shown in FIG. 24A, having a cut away section showing a top jaw member ribbon track and a suture retaining ribbon positioned therein, in accordance with the invention.

As illustrated in FIGS. 24A and 24B, the jaw mechanism 460 similarly comprises top and bottom jaw members 462, 464. As further illustrated in FIGS. 24A and 24B, the bottom jaw member 464 similarly comprises a guide channel 478 that is configured to receive a needle of the invention; preferably, needle 170 illustrated in FIG. 24E and discussed below, thereon, and a suture loading slot 472 that similarly allows a suture 71, to be loaded therein from either lateral side of the jaw mechanism 460, as illustrated in FIG. 24F, whereby the suture 71 can be engaged by the needle 170 as it slidably translates through guide channel 478, as illustrated in FIG. 24G.

Figure 24E:
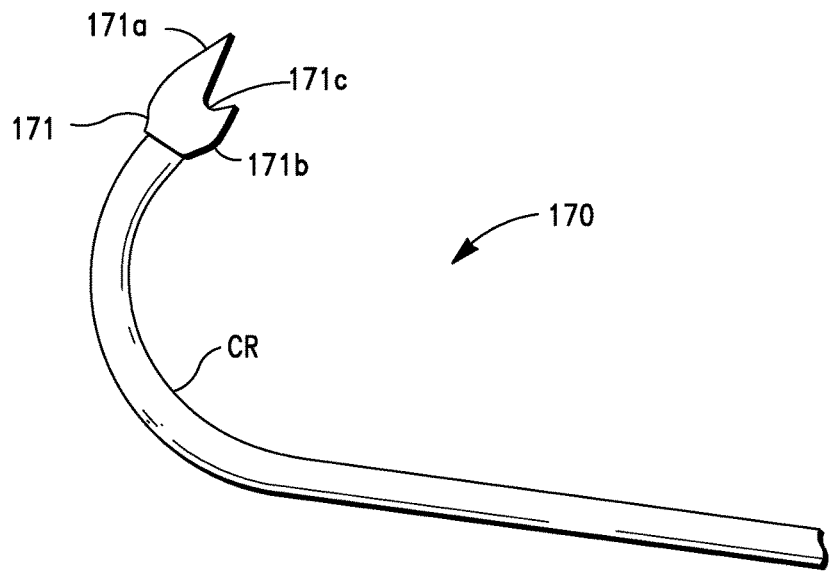
FIG. 24E is a partial perspective view of a system needle, in accordance with the invention.
Figure 24F:
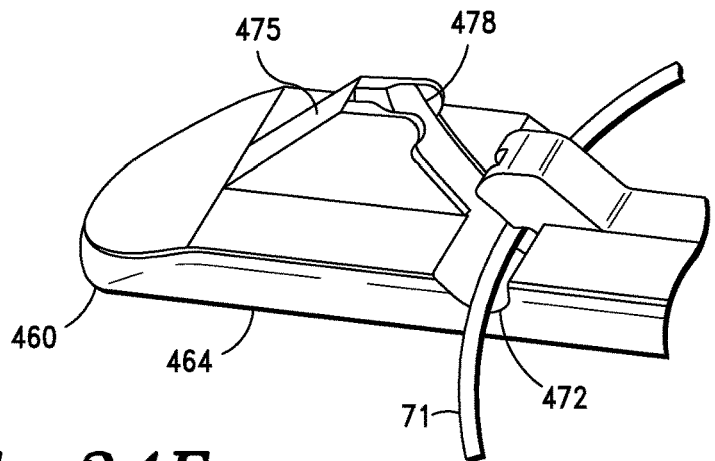
FIG. 24F is a partial perspective view of a bottom jaw member of the jaw mechanism shown in FIG. 24A, showing a suture positioned thereon, in accordance with the invention.
Figure 24G:
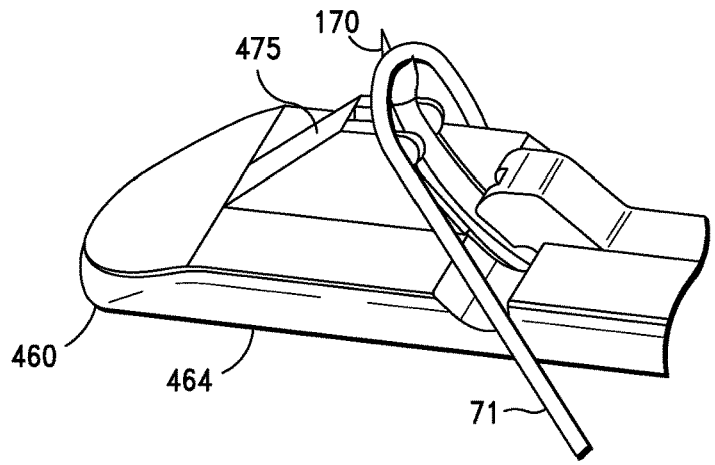
FIG. 24G is a further partial perspective view of the bottom jaw member FIG. 24F, showing the suture captured by the system needle shown in FIG. 24E, in accordance with the invention.

Referring now to FIG. 24E, there is shown a plan view of needle 170. As illustrated in FIG. 24E, the needle 170 comprises a suture ensnarement end 171 comprising a suture piercing region 171a and a suture retaining region 171b, the suture piercing region 171a and a suture retaining region 171b forming a suture seat 171c therebetween, which is configured to seat a suture therein, as illustrated in FIG. 24G.

As illustrated in FIG. 24E, the needle 170 further comprises a curvilinear region (denoted "CR") disposed on the distal end thereof.

In a preferred embodiment, the curvilinear portion "CR" of needle 170 comprises a bend radius that is in the range of approximately 10.0% to 80.0% greater than the track radius of the guide channel 478.

As illustrated in FIGS. 24B and 24C, in a preferred embodiment, the top jaw member 462 of the jaw mechanism 460 comprises a side wall opening 476 and hook 481, which facilitates suture capture in a surgical site.

As further illustrated in FIG. 24B, in a preferred embodiment, the bottom jaw member 464 comprises a raised suture guide region 475 proximate the distal end 473b of the jaw mechanism 460 and side wall opening 476, which is sized and configured to restrict access of a suture, e.g., suture 71, into the jaw mechanism 460 from the distal end 473b thereof and, hence, further facilitate suture capture from a lateral side of the jaw mechanism 460.

As further illustrated in FIGS. 24A and 24B, in one embodiment, the jaw mechanism 460 further comprises the aforementioned floating pivot mechanism (denoted "451").

In the noted embodiment, the floating pivot mechanism 451 thus comprises a first pin 453, which is sized and configured to be positioned in a first pin lumen (not shown) in the top jaw member 462, a second pin 455, which is sized and configured to be positioned in a second pin lumen 457 in the top jaw member 462, a third pin lumen in link 452, and a floating pin slot 456 in the bottom jaw member 464.

According to the invention, the floating pivot mechanism 451 operates in a similar manner and provides the same features and advantages as the floating pivot mechanism illustrated in FIGS. 8A and 8C, and discussed above.

Figure 25:
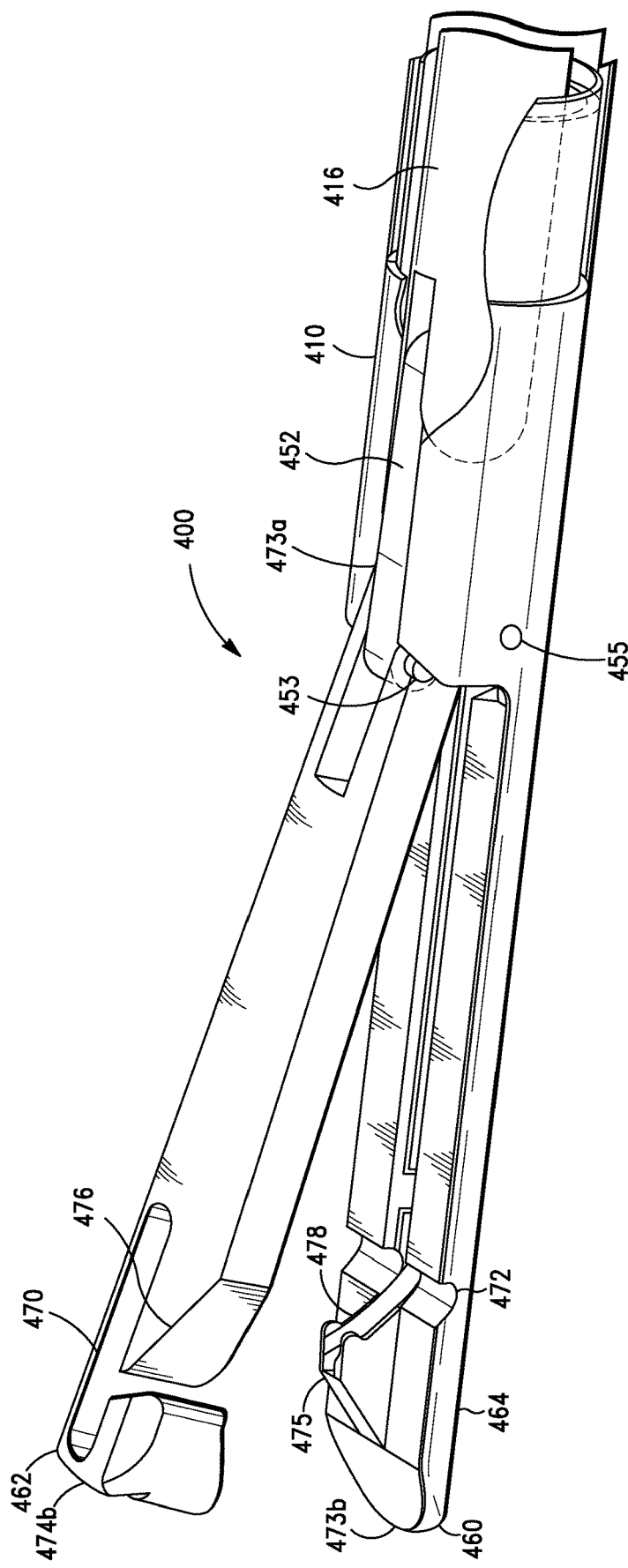
FIG. 25 is a partial perspective view of another embodiment of a jaw mechanism comprising a fixed pivot, in accordance with the invention.

Referring now to FIG. 25, in some embodiments, the jaw mechanism 460 comprises a simple pin 453 that defines a pivot point, wherein the top and bottom jaw members 462, 464 are in pivotal communication and the top jaw member 462 axially articulates with respect to the bottom jaw member 464.

As discussed in detail below, a seminal feature of the suture passing device 400 is the multifunction actuation system (denoted "405"), which is configured to provide at least the following synchronized functions during a single continuous rotational (or angular) articulation of trigger 406 from a default position, i.e., 0° rotation, to a fully actuated position: (i) articulation of the system jaw mechanism, in this instance, jaw mechanism 460, (ii) suture control, i.e., suture engagement, retainment and release, by the jaw mechanism 460, and (iii) translation and positioning of the device needle, in this instance, needle 170. The multifunction actuation system 405 is also configured to provide the same functions in reverse order during continuous rotational articulation of the trigger 406 from the fully actuated position to the default position, i.e., upon release of the trigger 406.

Figure 26:
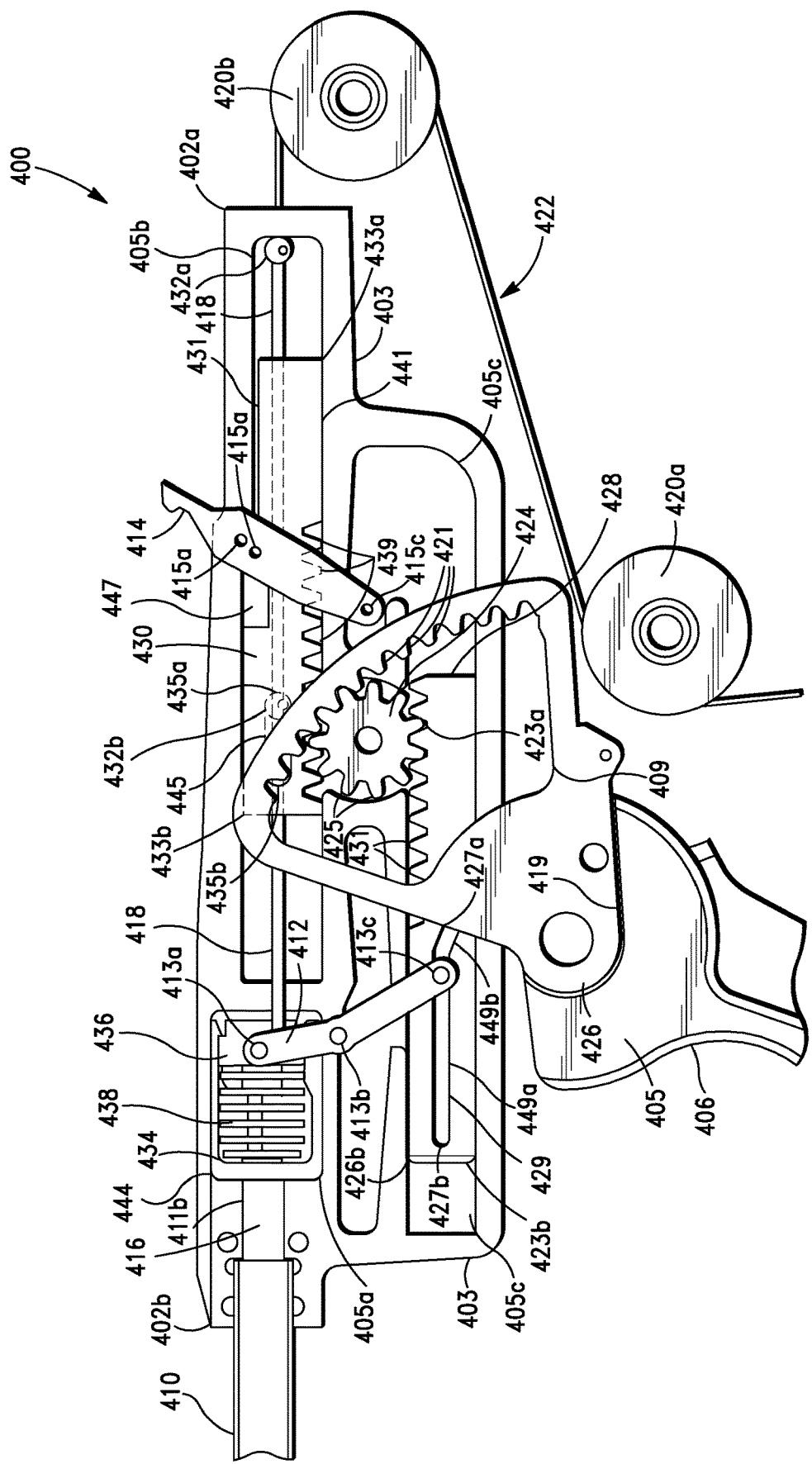
FIGS. 26 and 27 are side plan views of the suture passing device shown in FIG. 23, showing the jaw articulation system, suture control system, and needle articulation system of the suture passing device, in accordance with the invention.

Referring now to FIGS. 23 and 26, in one embodiment of the invention, the multifunction actuation system 405 comprises a trigger 406, a trigger arm/ring gear 426 and a pinion gear 424.

As illustrated in FIG. 26, the trigger arm/ring gear 426 is engaged to the proximal end 419 of the trigger 406 and comprises an open ring gear region 409 comprising a plurality of teeth 421 that are sized and configured to cooperate with the teeth 425 on the pinion gear 424, whereby rotational articulation of the trigger 406 induces rotation of the pinion gear 424.

Jaw Articulation

In a preferred embodiment, the suture passing system 400 comprises a jaw articulation system 444, which is adapted to cooperate with the multifunction actuation system 405 to provide articulation of the jaw mechanism 460 illustrated in FIG. 24A.

As illustrated in FIG. 26, the jaw articulation system 444 comprises a jaw rack 428, jaw lever 412, jaw driver 436 and jaw driver rod 416. In a preferred embodiment, the jaw rack 428 is sized and configured to be disposed in and slidably translate within the lower internal compartment 405c of the device frame 403.

As further illustrated in FIG. 26, in a preferred embodiment, the jaw rack 428 comprises a plurality of teeth 431 on the proximal end 423a, which are also sized and configured to cooperate with the teeth 425 on the pinion gear 424, and a jaw rack slot 429 on the distal end 423b of the jaw rack 428 that is sized and configured to receive pin 413c of the jaw lever 412, whereby the pin 413c is allowed to slidably translate within the jaw rack slot 429.

In a preferred embodiment, the jaw lever 412 is rotatably connected to the frame 403 of the suture passing device 400 via pin 413b, whereby rotational articulation of the trigger 406 induces linear translation of the jaw rack 428 and, thereby, rotation of the jaw lever 412 about pin 413b.

As further illustrated in FIG. 26, the jaw lever 412 is also rotatably connected to the jaw driver 436 (via pin 413a), which is coupled to the distal end 411b of the jaw drive rod 416, and the jaw drive rod 416 is coupled to the jaw driver 436 via a retaining ring 434.

In a preferred embodiment, the jaw articulation system 444 further comprises a jaw spring 438, which, as illustrated in FIG. 26, is positioned proximate the jaw driver 436 to accommodate variances in thickness of tissue being grasped by the jaw mechanism 460 and provide sufficient jaw mechanism closing force.

As further illustrated in FIG. 26, in some embodiments, the jaw rack slot 429 of the jaw rack 428 comprises an angled section 449b at the proximal end 427a of the jaw rack slot 429.

According to the invention, when the trigger 406 is initially rotationally articulated (or rotated) from an initial or default position, i.e., 0° rotation, which is illustrated in FIG. 23, toward handle 404, i.e., pulled inwardly, the jaw rack 428 is slidably translated toward proximal end 401a of the device 400, i.e., frame 403 thereof, wherein pin 413c translates through the angled section 449b the jaw rack slot 429, whereby the jaw lever 412 rotates (i.e., in a counterclockwise direction) and the jaw driver 436 and jaw drive rod 416 traverse toward the distal end 401b of the device frame 403 and induce a transition of the jaw mechanism 460 from its default open configuration to a closed configuration.

In a preferred embodiment, the trigger 406 is spring biased wherein, when the trigger 406 is released, the trigger 406 rotates away from the device handle 404 toward the default position, whereby the pinion gear 424 rotates in an opposite (i.e., clockwise) direction, whereby linear translation of the jaw rack 428, rotation of the jaw lever 412 about pin 413b and linear translation of the jaw driver 436 and jaw drive rod 416 coupled thereto are reversed and the jaw mechanism 460 transitions from the closed configuration to the default open configuration.

Articulation of the jaw mechanism 460 from an open configuration to a closed configuration is thus provided by the multifunction actuator 405 via rotational articulation of the trigger 406 in a first direction toward the device handle 404, and from the closed configuration to the open configuration via rotational articulation of the trigger 406 in a second direction away from the device handle 404, i.e., release of the trigger 406.

Suture Control

In a preferred embodiment, the suture passing system 400 further comprises a suture control system 413, which is also adapted to cooperate with the multifunction actuation system 405 to control suture engagement, retainment and release by the jaw mechanism 460.

Referring back to FIG. 24D, in a preferred embodiment, the suture control system 413 comprises an elongated suture retaining ribbon 450, which extends through the elongated shaft 410, into and through a ribbon slot 454 of the top jaw member 462, and across a window 470 disposed proximate the distal end 474b of the top jaw member 462, when the ribbon 450 is in an extended suture engagement position.

As discussed in detail below and illustrated in FIG. 24A, in a preferred embodiment, when the trigger 406 of the multifunction actuator 405 is in the default position, (i.e., 0° rotation) illustrated in FIG. 23, the suture retaining ribbon 450 is in the extended suture engagement position, whereby a suture, e.g., suture 71, cannot be drawn through the window 470 of the top jaw member 462 by a system needle.

When the trigger 406 is rotationally articulated toward the device handle 404, at the proper sequenced timing, the suture retaining ribbon 450 is retracted from jaw member window 470, as illustrated in FIG. 24D, whereby a suture can be drawn through the window 470 of the top jaw member 462 by a system needle. Thereafter, when the trigger 406 is rotationally articulated away from the device handle 404, i.e., released, the suture retaining ribbon 450 is advanced and extends across the jaw member window 470 to the suture engagement position, whereby the suture retaining ribbon 450 engages the suture and draws the suture toward a distal wall 477 of the jaw member window 470, wherein the suture is positioned on and retained against the distal wall 477 of jaw member window 470.

As illustrated in FIGS. 24C and 24D, in a preferred embodiment, the distal wall 477 of jaw member window 470 comprises a recess 479 adapted to receive the suture, whereby, when the suture retaining ribbon 450 engages the suture and draws or pushes the suture toward a distal wall 477 of the jaw member window 470, the suture seats in the recess 479 in the distal wall 477 and creates a strain relief to promote greater retention capacity of the suture.

According to the invention, when a suture is retained by the suture retaining ribbon 450 of the suture control system 413, the suture can be manipulated by an operator of the device 400 in a surgical site to construct a desired stitch pattern, such as one of the aforementioned stitch patterns.

As discussed below, according to the invention, the suture retaining ribbon 450 can also be retracted in the ribbon slot 454 of the top jaw member 462 by the operator to release a suture disposed in the jaw member window 470 and, hence, jaw mechanism 460. The suture can be recaptured and drawn into the jaw member window 470 thereafter by the jaw mechanism 460 via the side wall opening 476 in the top jaw member 462 for retainment by the suture retaining ribbon 450 to continue constructing a desired stitch pattern.

Figure 27:
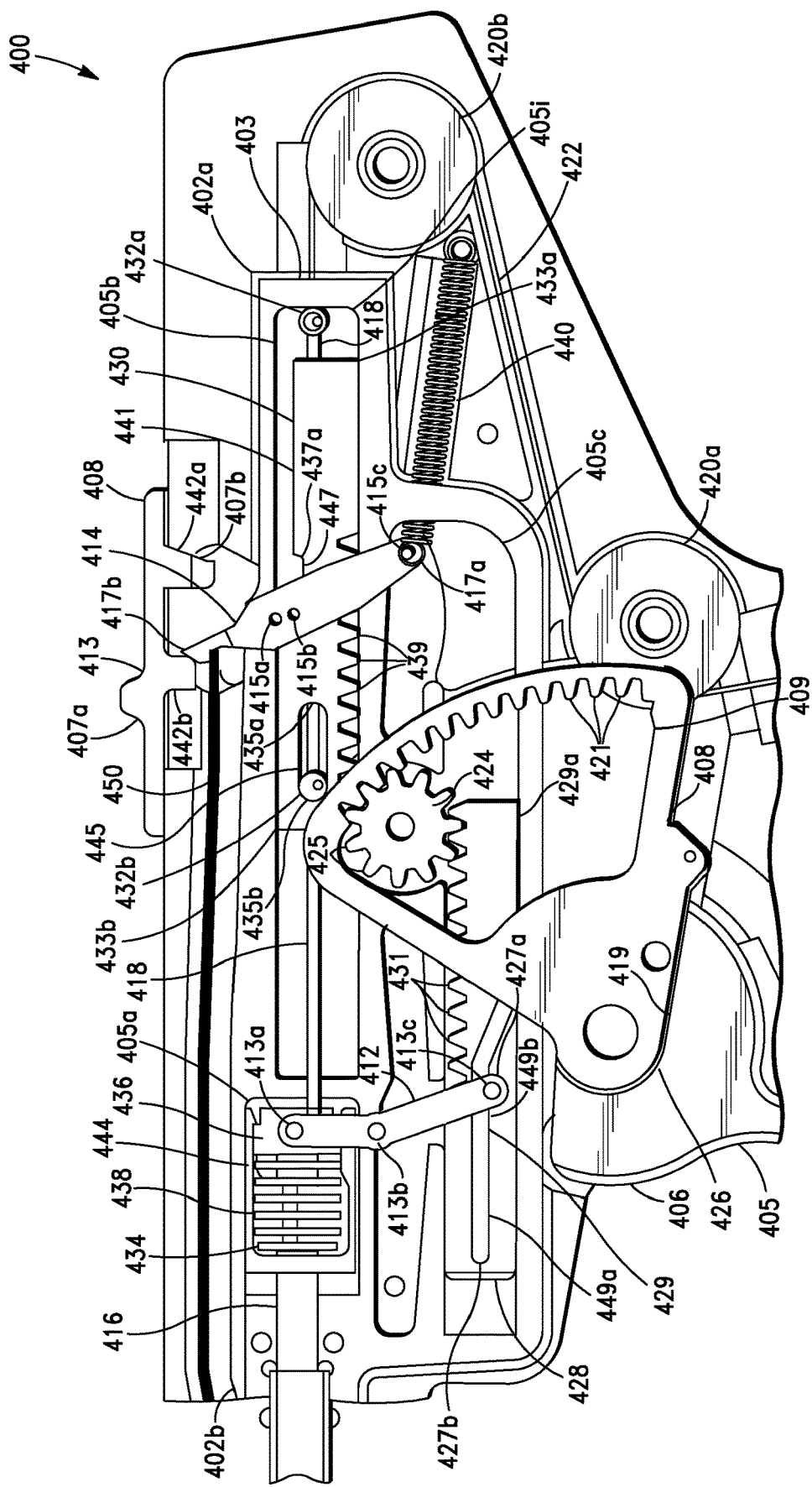

Referring now to FIGS. 26 and 27, the suture control system 413 further comprises a capture lever 414 and suture control switch 408, which, as also discussed in detail below, is configured and adapted to modulate suture retaining ribbon 450 translation and, thereby, suture engagement, retainment and release.

Figure 28:
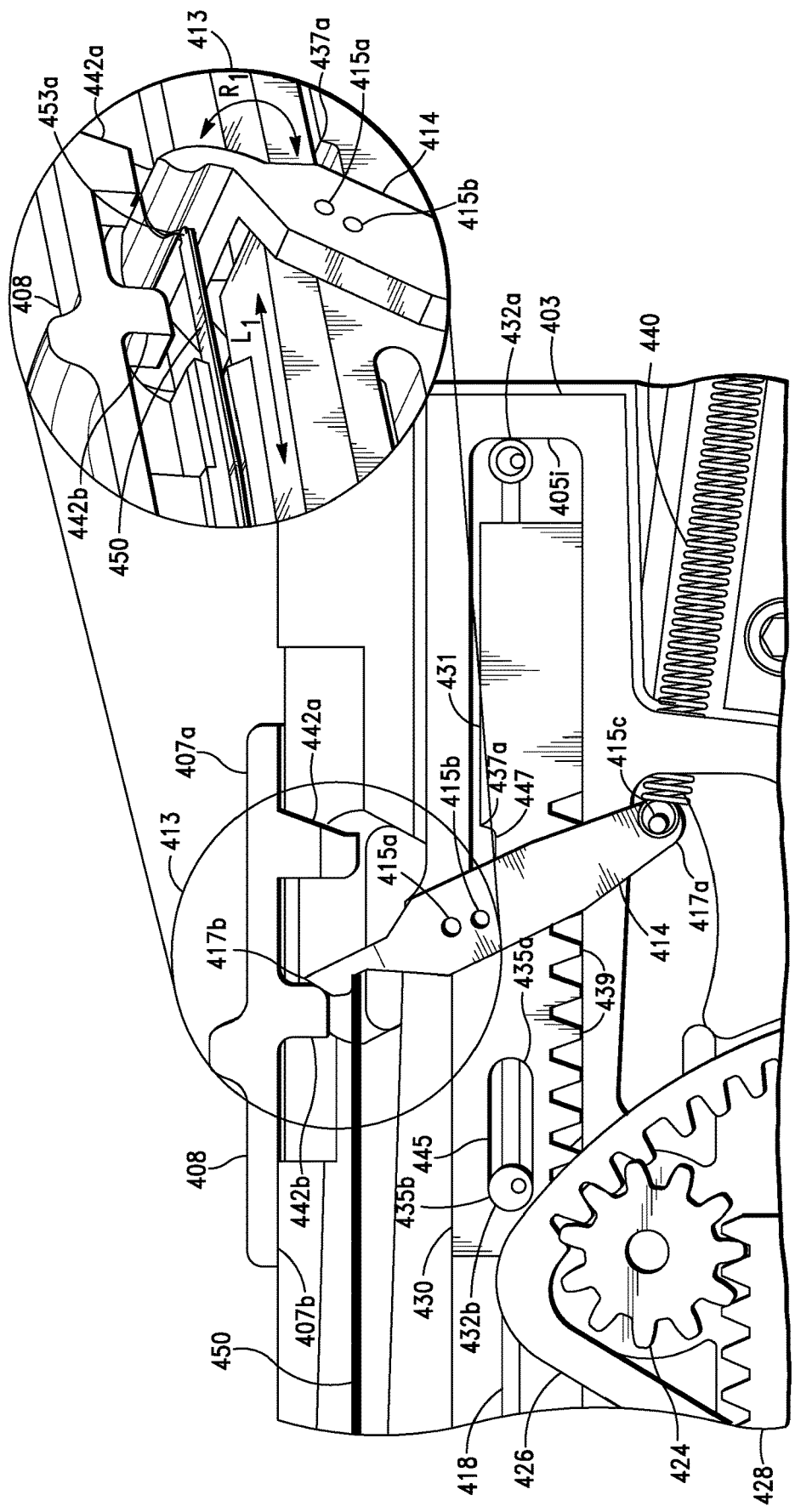
FIG. 28 is a partial side plan view of the suture passing device shown in FIG. 23, showing the suture control system of the device, in accordance with the invention.

As illustrated in FIGS. 27 and 28, in a preferred embodiment, the suture retaining ribbon 450 is engaged to the distal end 417b of the capture lever 414.

As further illustrated in FIGS. 27 and 28, the capture lever 414 is rotatably engaged to the frame 403 via pin 415a and the proximal end 417a of the capture lever 414 is coupled to capture lever spring 440 via pin 415c.

According to the invention, the pin 415a defines a pivot point on the frame 403 and, as illustrated in FIG. 28, converts rotational movement of the capture lever 414 (denoted by arrow "$R_1$") to slidable translation of the ribbon 450 towards the proximal end 402a or distal end 402b of the device frame 403 (denoted by arrow "$L_1$").

Figure 29B:
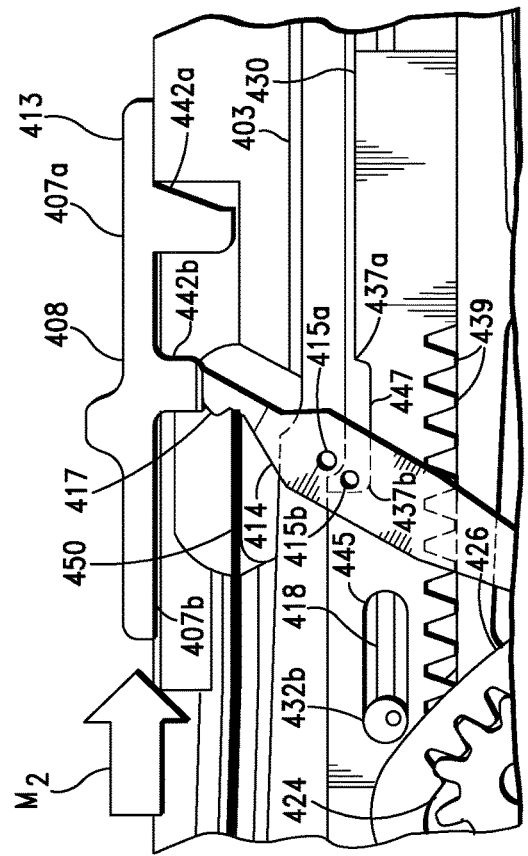
FIG. 29B is a further partial side plan view of the suture passing device shown in FIG. 23, showing the suture control switch of the device positioned in a no-engagement mode, in accordance with the invention.
Figure 29A:
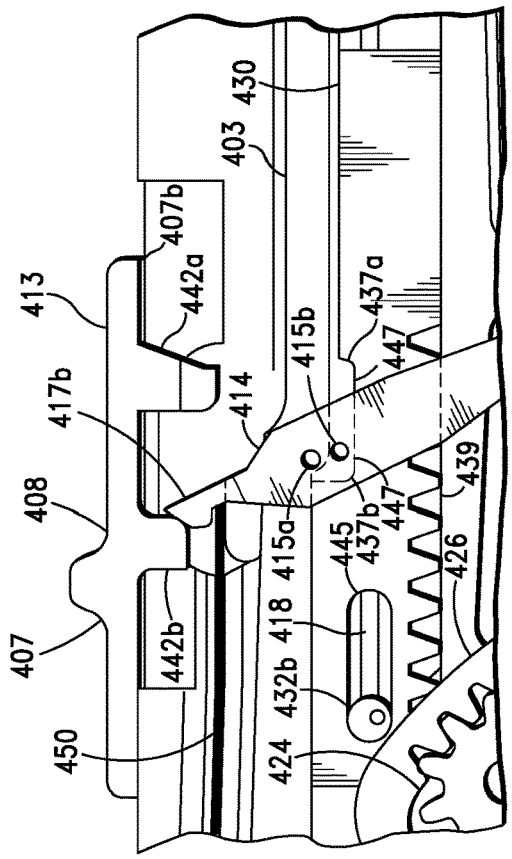
FIG. 29A is a further partial side plan view of the suture passing device shown in FIG. 23, showing the suture control switch of the device positioned in an auto-engagement mode, in accordance with the invention.

As further illustrated in FIG. 27, the distal end 417b of the capture lever 414 is sized and configured to abut tabs 442a, 442b disposed on the bottom surface 407b of the suture control switch 408 (see also FIGS. 29A and 29B).

Referring back to FIG. 26, the capture lever 414 is also adapted to communicate with the needle rack 430 via pin 415b, which, as discussed below, is sized and configured to abut the proximal end 437a of the needle rack recess 447 in the needle rack 430, when the needle rack 430 translates toward the distal end 402b of the device frame 403.

As further illustrated in FIGS. 27 and 28, the proximal end (or lip) 437a of the needle rack recess 447 is preferably positioned a predetermined dwell distance from pin 415b of the capture lever 414, whereby the capture lever 414 is initially stationary, i.e., suture control system 413 is in dwell.

As indicated above, in a preferred embodiment, when the trigger 406 of the multifunction actuator 405 is in the default position, (i.e., 0° rotation), the suture retaining ribbon 450 is in an extended position, whereby a suture cannot be drawn through the window 470 of the top jaw member 462 by a system needle.

During initial rotational articulation of the system trigger 406 toward the handle 404, the needle rack 430 translates toward the distal end 402b of the device frame 403 until pin 415b abuts the proximal end (or lip) 437a of the needle rack recess 447 (i.e., the suture control system 413 is in dwell). During further rotation of the system trigger 406 toward the handle 404 and, thereby, further translation of the needle rack 430 toward the distal end 402b of the device frame 403 (after pin 415b abuts the proximal end 437a of the needle rack recess 447), clockwise rotation ($R_1$) of the capture lever 414 is induced (as illustrated in FIG. 26), which retracts the suture retaining ribbon 450 toward the proximal end 402a of the device frame 403, and, hence, proximal end 473a of the jaw mechanism 460, whereby a suture, in this instance, suture 71 can be drawn into the jaw member window 470.

When the trigger 406 is rotationally articulated away from the device handle 404, i.e., is released, the needle rack 430 translates toward the proximal end 402a of the device frame 403 and the capture lever 414 rotates in a counterclockwise direction, wherein the suture retaining ribbon 450 advances, engages the suture 71 and retains the suture 71 in the jaw member window 470.

During translation of the needle rack 430 toward the distal end 402b of the device frame 403, pin 415b the capture lever 414 sits on and translates over the top proximal surface 431 of the needle rack 430, i.e., the top proximal surface 431 of the needle rack 430 functions as a dwell feature to maintain the capture lever 414 in a stationary state, whereby the suture retaining ribbon 450 is maintained in the retracted position while the needle advances the suture.

As indicated above and illustrated in FIG. 28, in a preferred embodiment, the proximal end 417a of the capture lever 414 is coupled to capture lever spring 440, which is adapted to rotatably bias the capture lever 414 in a counterclockwise direction, whereby the suture retaining ribbon 450 is extended forward in slot 454 and across the jaw member window 470.

As indicated above and illustrated in FIGS. 23 and 27, in a preferred embodiment, the suture control system 413 further comprises a suture control switch 408, which is adapted to modulate suture engagement, more specifically, control engagement of and interaction between the suture retaining ribbon 450 and suture 71.

As illustrated in FIG. 28, the distal end 417b of the capture lever 414 is sized and configured to abut tabs 442a, 442b disposed on the bottom surface 407b of the suture control switch 408 to facilitate communication by and between the capture lever 414 and the suture control switch 408.

As discussed in detail below, the suture control switch 408 enables an operator to interact with and modulate the position of the capture lever 414 and, thereby, set the suture control function of the suture control system 413 and, hence, suture passing device 400 between two (2) modes: (1) an "auto-engagement" mode, i.e., engagement and, thereby, interaction of the suture retaining ribbon 450 with the suture 71, which is illustrated in FIG. 29A, and a (2) "no-engagement" mode, i.e., no engagement of ribbon 450 to suture 71, and, hence, no interaction therebetween, as illustrated in FIG. 29B.

As illustrated in FIGS. 29A and 29B, in a preferred embodiment, an operator can manually translate (or move) the suture control switch 408, i.e., advance or retract the switch 408 in a linear direction, along the top surface 407a of the suture passing device body 402 to switch the suture control system 413 from the "auto-engagement" mode (i.e., first switch position illustrated in FIG. 29A) to the "no-engagement" mode (i.e., second switch position illustrated in FIG. 29B), as denoted by arrow "$M_2$", and from the "no-engagement" mode to the "auto-engagement" mode.

Referring back to FIGS. 24D and 27, the ribbon 450 extends from the capture lever 414 through the elongated shaft 410 and into and through the ribbon slot 454 of the top jaw member 462, and, when extended, across jaw member window 470 disposed proximate the distal end 474b of the top jaw member 462.

According to the invention, when the trigger 406 of the multifunction actuator 405 is in the default position, i.e., at 0° of rotation, and the suture control system 413 is in "auto-engagement" mode illustrated in FIG. 29A, the capture lever 414 is preferably spring biased in a fully rotated counterclockwise direction, as illustrated in FIGS. 27 and 28, whereby the suture retaining ribbon 450 is fully advanced through the elongated shaft 410, into and through the ribbon slot 454 of the top jaw member 462, and across the jaw member window 470.

According to the invention, when the suture control system 413 is in "auto-engagement" mode and the trigger 406 of the multifunction actuator 405 is rotated a first defined angle, e.g., between 5.0° to 15.0°, from the default position, as indicated above, the distal end 417b of the capture lever 414 is rotated in a clockwise direction, wherein the suture retaining ribbon 450 is retracted from the jaw member window 470 and, thereby, allows the needle 170 with suture 71 attached thereto to traverse therethrough.

After the needle 170 has passed a suture 71 into and through biological tissue and through the jaw member window 470, the trigger 406 is rotated away from the handle 404, i.e., is released, whereby the trigger 406 and, hence, multifunction actuator 405 return to the default position, i.e., 0° of rotation.

As indicated above, when the trigger 406 returns to the default position, the capture lever 414 rotates (i.e., in a counterclockwise direction), the suture retaining ribbon 450 is advanced through the elongated shaft 410, into and through the ribbon slot 454 of the top jaw member 462, and across the jaw member window 470, whereby the suture retaining ribbon 450 engages the suture 71 and draws the suture 71 toward and retains the suture 71 in the jaw member window 470.

As set forth below, according to the invention, the suture control switch 408 can also be manually moved to the "no-engagement" position illustrated in FIG. 29B to disengage the suture retaining ribbon 450 from the suture 71 and, hence, release the suture 71.

Referring to FIG. 29B, when the suture control switch 408 is manually moved to the "no-engagement" position, the distal tab member 442b of the switch 408 contacts the distal end 417b of the capture lever 414 and rotates the capture lever 414 in a clockwise direction, whereby the suture retaining ribbon 450 retracts from the jaw member window 470 and disengages from the suture 71, wherein the suture 71 is released from the distal wall 477 of the jaw member window 470.

As illustrated in FIG. 29B, in a preferred embodiment, the distal tab member 442b is sized and configured to contact the distal end 417b of the capture lever 414, whereby the capture lever 414 is locked in the "no-engagement" position and the suture retaining ribbon 450 is thereby locked in a retracted position. Rotation of the capture lever 414 and, hence, translation of the suture retaining ribbon 450 through the jaw member slot 454 and window 470 is also abated.

According to the invention, the suture control switch 408 can subsequently be manually moved from the "no-engagement" mode to the "auto-engagement" mode to unlock the capture lever 414 and allow translation of the suture retaining ribbon 450 through the jaw member slot 454 and window 470, i.e., release the ribbon 450 from its retracted position.

Control of a suture, i.e., ensnarement, retainment and release, can thus also be effectuated by the multifunction actuator 405 via simple rotational articulation of the trigger 406.

Needle Articulation

In a preferred embodiment, the suture passing system 400 further comprises a needle articulation system 441, which is also adapted to cooperate with the multifunction actuation system 405 to induce and control articulation of the system needle; preferably, needle 170 illustrated in FIG. 24E.

Referring back to FIG. 26, in addition to needle 170, the needle articulation system 441 comprises a needle rack 430, needle support tube 418, which is sized and configured to receive the needle 170 therein, and proximal and distal needle holders 432a, 432b, which are coupled to the needle support tube 418.

In a preferred embodiment, the needle rack 430 is sized and configured to be disposed in and slidably translate within the upper internal compartment 405b of the device frame 403. As also illustrated in FIG. 26, the needle rack 430 further comprises a plurality of teeth 439 on the distal end 433b of the needle rack 430, which are also sized and configured to cooperate with the teeth 425 on the pinion gear 424.

As further illustrated in FIG. 26, the needle rack 430 further comprises a needle rack slot 445 that is sized and configured to receive the distal needle holder 432b, whereby, as discussed below, the distal needle holder 432b is allowed to slidably translate therein and provide a needle articulation system 441 dwell, i.e., a predetermined distance and, hence, delay in function.

In a preferred embodiment, the proximal needle holder 432a is coupled to the needle support tube 418 and needle 170 and is positioned in the upper internal compartment 405b of the device frame 403, whereby, upon rotational articulation of the trigger 406 toward the handle 404 and, thereby, linear translation of the needle rack 430 (and, thereby, needle support tube 418 and needle 170), the proximal needle holder 432a abuts a proximal interior wall 405i of the device frame 403 and functions as a positive stop for the needle support tube 418 and needle 170, and, hence, needle translation.

As further illustrated in FIG. 26, in a preferred embodiment, the proximal needle holder 432a is coupled to a needle assembly cable 422, which is sized to be drawn across two (2) pulley members 420a, 420b and coupled to a return spring (not shown) that provides tension to retract the needle 170 to a default retracted position when the trigger 406 is released from a fully actuated position.

In a preferred embodiment, during rotational articulation of the trigger 406 toward the handle 404, the needle rack 430 and, thereby, needle support tube 418 (and, hence, needle 170 disposed therein) remain stationary, i.e., needle articulation system in dwell until the distal needle holder 432b abuts a proximal end region 435a of the needle rack slot 445, and, thereafter, during further rotational articulation of the trigger 406 (i.e., toward the handle 404), needle rack 430 and, thereby, needle support tube 418 and needle 170 advance toward the distal end 402b of the device frame 403 and the needle 170, advances out of the elongated shaft 410.

In a preferred embodiment, during rotational articulation of the trigger 406 away from the handle 404, i.e., upon release of the trigger 406, the needle rack 430 and, thereby, needle support tube 418 and needle 170, advance toward the proximal end 402a of the device frame 403 and the needle 170 retracts into the elongated shaft 410.

According to the invention, articulation of the needle 170 is thus also provided by the multifunction actuator 405 via simple rotational articulation of the trigger 406.

As reflected in FIG. 30, the multifunction actuation system 405 of suture passing device 400 thus sequentially (i) articulates and positions the system jaw mechanism, in this instance, jaw mechanism 460, (ii) controls the ensnarement, retainment and release of a suture, and (iii) articulates and positions the system needle, in this instance, needle 170 during continuous rotational articulation of the trigger 406 from a default position, i.e., 0° rotation, toward the device handle 404 to a fully actuated position, and sequentially provides the same functions in reverse order during continuous rotational articulation of the trigger 406 from the fully actuated position to the default position, i.e., upon release of the trigger 406.

As further reflected in FIG. 30, the noted functions are provided during six (6) distinct stages of the noted articulations of the system trigger 406.

Figure 31B:
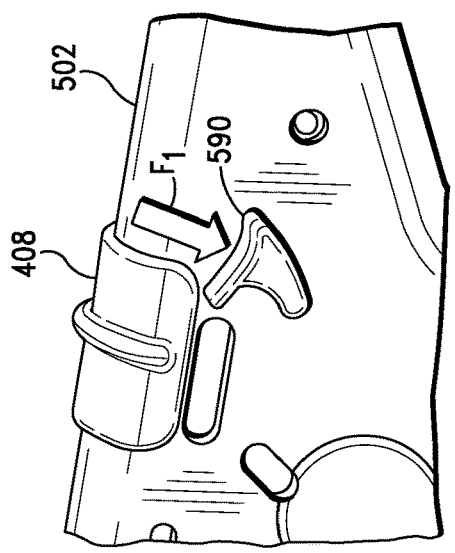
FIG. 31B is a partial perspective view of the suture passing device shown in FIG. 31A, showing a suture release tab in a default position, in accordance with the invention.
Figure 31C:
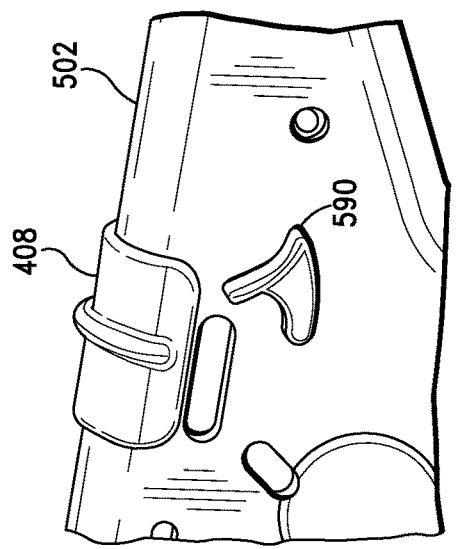
FIG. 31C is a further partial perspective view of the suture passing device shown in FIG. 31A, showing the suture release tab in an actuated position, in accordance with the invention.
Figure 31A:
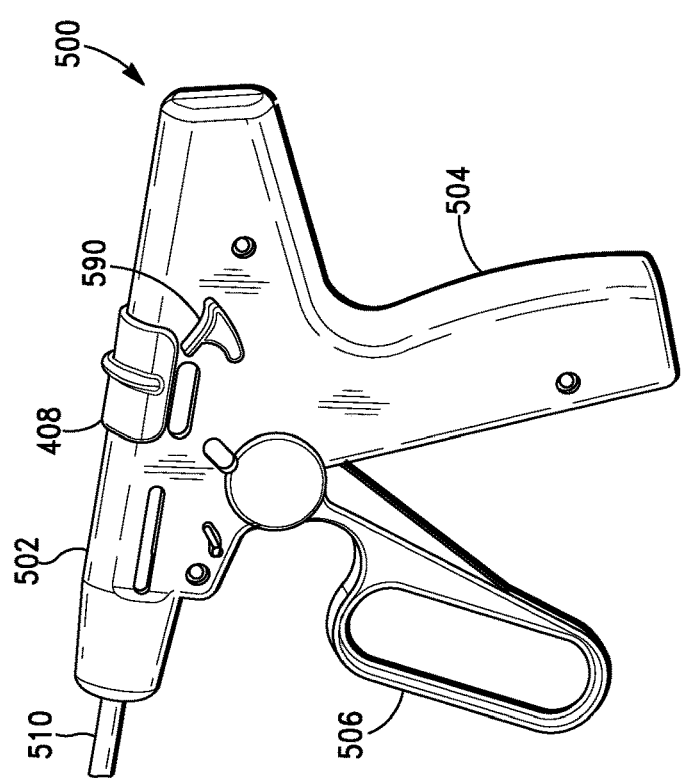
FIG. 31A is a perspective view of another embodiment of the suture passing device, in accordance with the invention.

Referring now to FIG. 31A, there is shown another embodiment of suture passing device 400 (now denoted "500"), which similarly comprises a multifunction actuation system 505 that is configured to similarly provide at least the following synchronized functions during a single continuous rotational (or angular) articulation of the system trigger from a default position, i.e., 0° rotation to a fully actuated position: (i) articulation of the system jaw mechanism, (ii) suture control, i.e., suture engagement, retainment and release, by the jaw mechanism, and (iii) translation and positioning of the device needle. The multifunction actuation system 505 is similarly also configured to provide the same functions in reverse order during continuous rotational articulation of the system trigger from the fully actuated position to the default position.

As illustrated in FIG. 31A, the suture passing device 500 thus similarly comprises a body 502, handle 504 and an elongated member or shaft 510. In a preferred embodiment, the elongated member shaft 510 similarly includes jaw mechanism 460, whereby the suture passing device 500 similarly comprises aforementioned features and advantages associated therewith.

Figure 32:
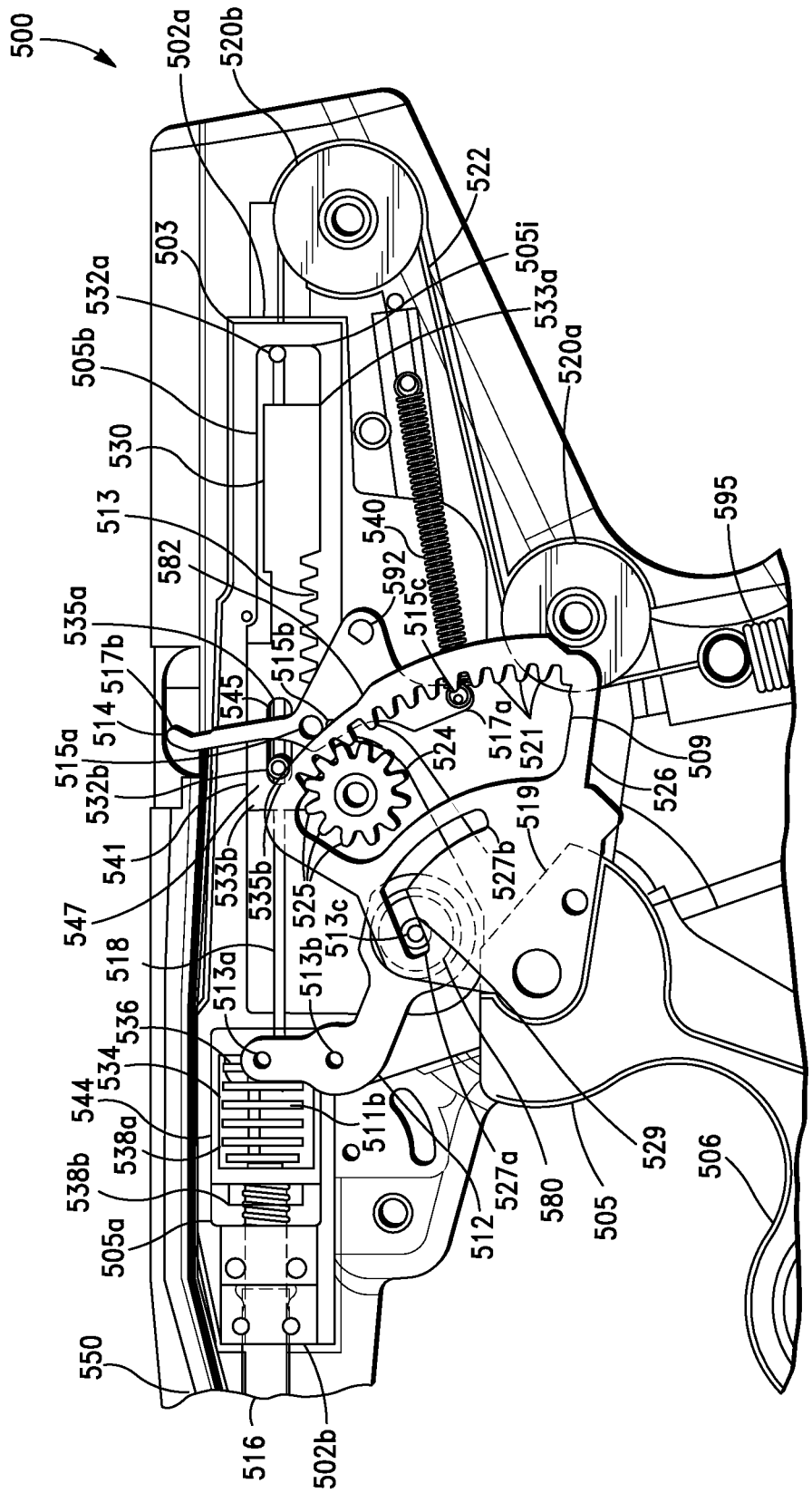
FIG. 32 is a side plan view of the suture passing device shown in FIG. 31A, showing the jaw articulation system, suture control system, and needle articulation system of the device, in accordance with the invention.

Referring now to FIG. 32, in a preferred embodiment, the multifunction actuation system 505 similarly comprises a trigger 506, a trigger arm/ring gear 526 and a pinion gear 524.

As illustrated in FIG. 32, the trigger arm/ring gear 526 is similarly engaged to the distal end 519 of the trigger 506 and comprises an open ring gear region 509 comprising a plurality of teeth 521 that are sized and configured to cooperate with the teeth 525 on the pinion gear 524, whereby rotational articulation of the trigger 506 induces rotation of the pinion gear 524.

As further illustrated in FIG. 32, the trigger arm/ring gear 526 comprises an outer ring gear surface 582, which is radially concentric with the rotational articulation of the trigger arm/ring gear 526, and preferably includes a first region 531a, a second region 531b and a third region 531c.

In a preferred embodiment, the trigger arm/ring gear 526 is also coupled to jaw lever 512 and the jaw lever bearing 580 associated therewith via pin 513c.

In a preferred embodiment, the trigger arm/ring gear 526 further comprises a ring gear slot 529 that is sized and configured to receive pin 513c therein and allow the pin 513c to translate therethrough.

As further illustrated in FIG. 32, the jaw lever 512 is also rotatably coupled to the frame 503 via pin 513b and, as discussed below, the jaw driver 536 via pin 513a.

Jaw Articulation

In a preferred embodiment, the suture passing system 500 similarly comprises a jaw articulation system 544, which is adapted to cooperate with the multifunction actuation system 505 to provide articulation of the jaw mechanism 460.

As illustrated in FIG. 32, the jaw articulation system 544 comprises a jaw driver 536 that is sized and configured to be seated in and slidably translate within compartment 505a of the device frame 503.

In a preferred embodiment, the jaw driver 536 comprises a distal opening that is sized and configured to receive the distal end 511b of jaw drive rod 516, which is disposed inside the elongated member 510. As illustrated in FIG. 32, the distal end 511b of the jaw drive rod 516 is preferably coupled to the jaw driver 536.

As further illustrated in FIG. 32, in a preferred embodiment, the jaw articulation system 544 similarly comprises a jaw spring 538a that is sized and configured to accommodate the dimensional variance of any article, e.g., biological tissue, disposed between top and bottom jaw members 462, 464 of the jaw mechanism 460 (e.g., various thicknesses of biological tissue), and provide adequate clamping force of the jaw mechanism 460.

As further illustrated in FIG. 32, in a preferred embodiment, the jaw articulation system 544 further comprises a jaw return spring 538b that is disposed on the distal end 511b of the jaw drive rod 516 proximate the jaw driver 536. In a preferred embodiment, jaw return spring 538b is sized and configured to bias or preload the jaw driver 536 to a default position.

As indicated above and illustrated in FIG. 32, the jaw lever 512 is coupled to the jaw driver 536 via pin 513a and to the frame 503 via pin 513b, which defines a pivot point on the frame 503 that converts rotational movement of the jaw lever 512 to slidable translation of the jaw driver 536 within compartment 505a of device frame 503.

As also indicated above, in a preferred embodiment, the trigger arm/ring gear 526 comprises a ring gear slot 529 that is sized and configured to receive pin 513c therein and allow the pin 513c to translate therethrough.

In a preferred embodiment, the jaw lever 512 comprises a jaw lever bearing 580 in communication with the pin 513c to reduce frictional forces that are generated when the pin 513c slidably translates within the ring gear slot 529 of the trigger arm/ring gear 526.

As illustrated in FIG. 32, in a preferred embodiment, the ring gear slot 529 comprises a linear region 527a (or first segment of a cam path) and a radial region 527b (or second segment of the cam path). According to the invention, when the pin 513c is disposed in the ring gear slot 529 and the trigger 506 is initially rotationally articulated (or rotated) in a first direction from a default toward the device handle 504, i.e., pulled inwardly, pin 513c slidably translates through the linear region 527a of the ring gear slot 529 and induces counterclockwise rotation of the jaw lever 512, and, thereby, translation of the jaw driver 536 within compartment 505a toward the distal end 502b of the device frame 503, wherein the jaw mechanism 460 similarly transitions from the default open configuration to the closed configuration.

When the trigger 506 is further rotated toward the handle 504 (e.g., the trigger is rotated approx. 8.4°), the pin 513c translates from the linear region 527a to the radial region 527b of the ring gear slot 529, whereby the jaw lever 512 and, thereby, jaw driver assembly 536 (and, hence, jaw driver 537) cease linear translation and remain in a constant fixed position, wherein the jaw mechanism 460 is maintained in the closed configuration, i.e., jaw articulation system 544 in dwell.

In a preferred embodiment, the trigger 506 is similarly spring biased wherein, when the trigger 506 is released, the trigger rotates away from the device handle 504, i.e., toward the initial or default position illustrated in FIG. 31A, whereby the pin 513c translates back through the radial region 527b of the ring gear slot 529 and into and through the linear region 527a of the ring gear slot 529, wherein clockwise rotation of the jaw lever 512 is induced, and, thereby, translation of the jaw driver 536 within compartment 505a toward the proximal end 502a of the device frame 503, wherein the jaw mechanism 460 similarly transitions from the closed configuration to the default open configuration.

As indicated above, the jaw return spring 538b biases the jaw driver 536 back to a default position to maintain the jaw mechanism 460 in the default open configuration.

Articulation of the jaw mechanism 460 from an open configuration to a closed configuration is thus similarly provided by multifunction actuator 505 of suture passing system 500 via rotational articulation of the system trigger 506 in a first direction toward the device handle 504, and from the closed configuration to the open configuration via rotational articulation of the trigger 506 in a second direction away from the device handle 504, i.e., release of the trigger 506.

Suture Control

In a preferred embodiment, the suture passing system 500 similarly further comprises a suture control system 513, which is also adapted to cooperate with the multifunction actuation system 505 to control suture engagement, retainment and release by the jaw mechanism 460.

In a preferred embodiment, the suture control system 513 similarly comprises an elongated suture retaining ribbon (denoted "550" in this embodiment), which similarly extends into and through the jaw mechanism 460, as described above, and suture control switch 408.

Figure 33:
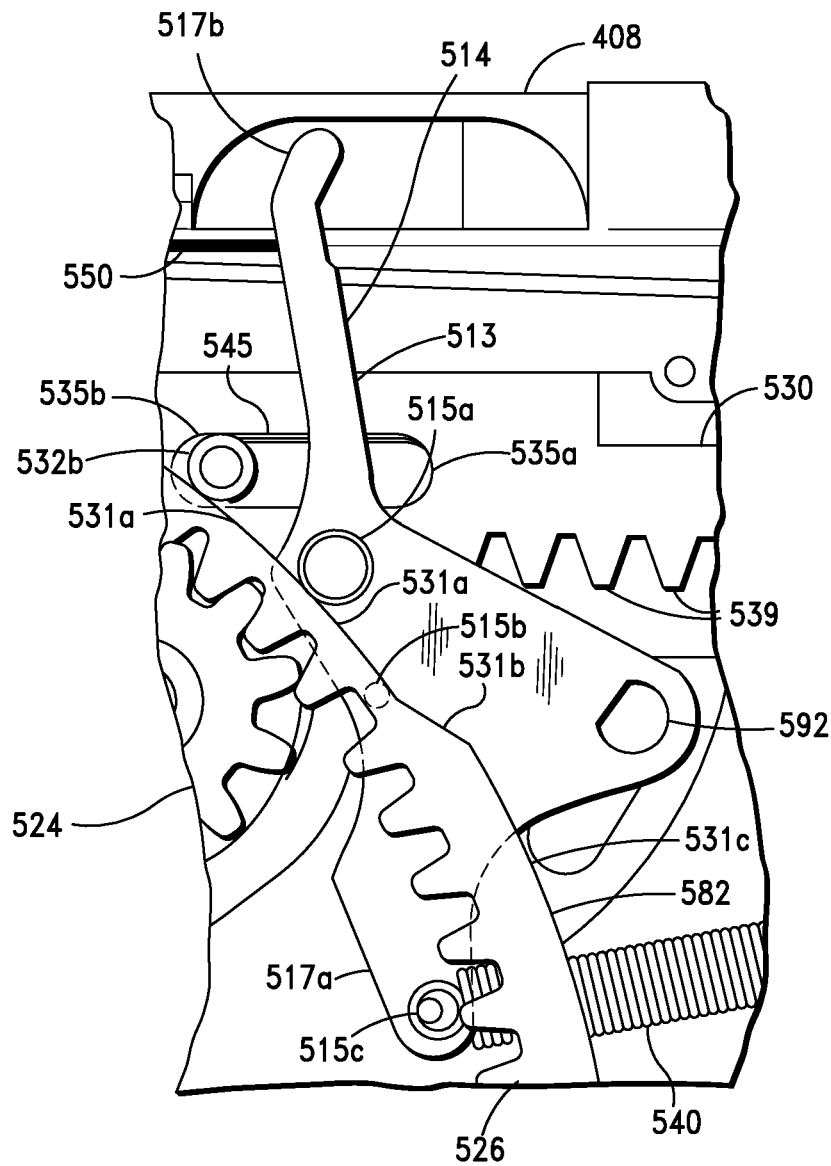
FIG. 33 is a partial side plan view of the suture passing device shown in FIG. 31A, showing the suture control system shown in FIG. 32, in accordance with the invention.

As illustrated in FIGS. 32 and 33, the suture control system 513 further comprises a capture lever 514, which is rotatably engaged to the frame 503 via pin 515b. As further illustrated in FIGS. 32 and 33, suture capture ribbon 550 is attached to the distal end 517b of the capture lever 514 and the proximal end 517a of the capture lever 514 is coupled to capture lever spring 540 via pin 515c.

According to the invention, pin 515b similarly defines a pivot point on the frame 503 and, thus, similarly converts rotational movement of the capture lever 514 to slidable translation of the suture retaining ribbon 550 towards the proximal end 502a or distal end 502b of the device frame 503.

As further illustrated in FIGS. 32 and 33, and discussed in detail below, the capture lever 514 is also in communication with the trigger arm/ring gear 526 via pin 515a, which is sized and configured to abut and traverse over the outer ring gear surface 582 of the trigger arm/ring gear 526.

The trigger arm/ring gear 526 is similarly in communication with the pinion gear 524, wherein, when the trigger 506 is rotationally articulated in a first direction from a default position toward the device handle 504, i.e., pulled inwardly, the trigger arm/ring gear 526 rotates, which slidably translates pin 515a of the capture lever 514 along outer ring gear surface 582 of the trigger arm/ring gear 526, and, as discussed above, also advances the jaw lever 512 and, thereby, jaw driver 536 and jaw driver rod 516.

According to the invention, when the trigger 506 of the multifunction actuator 505 is in the default position (i.e., 0° rotation) illustrated in FIG. 31A, the suture retaining ribbon 550 is similarly in an extended position, whereby a suture cannot be drawn through the window 470 of the top jaw member 462 by a system needle.

Figure 34:
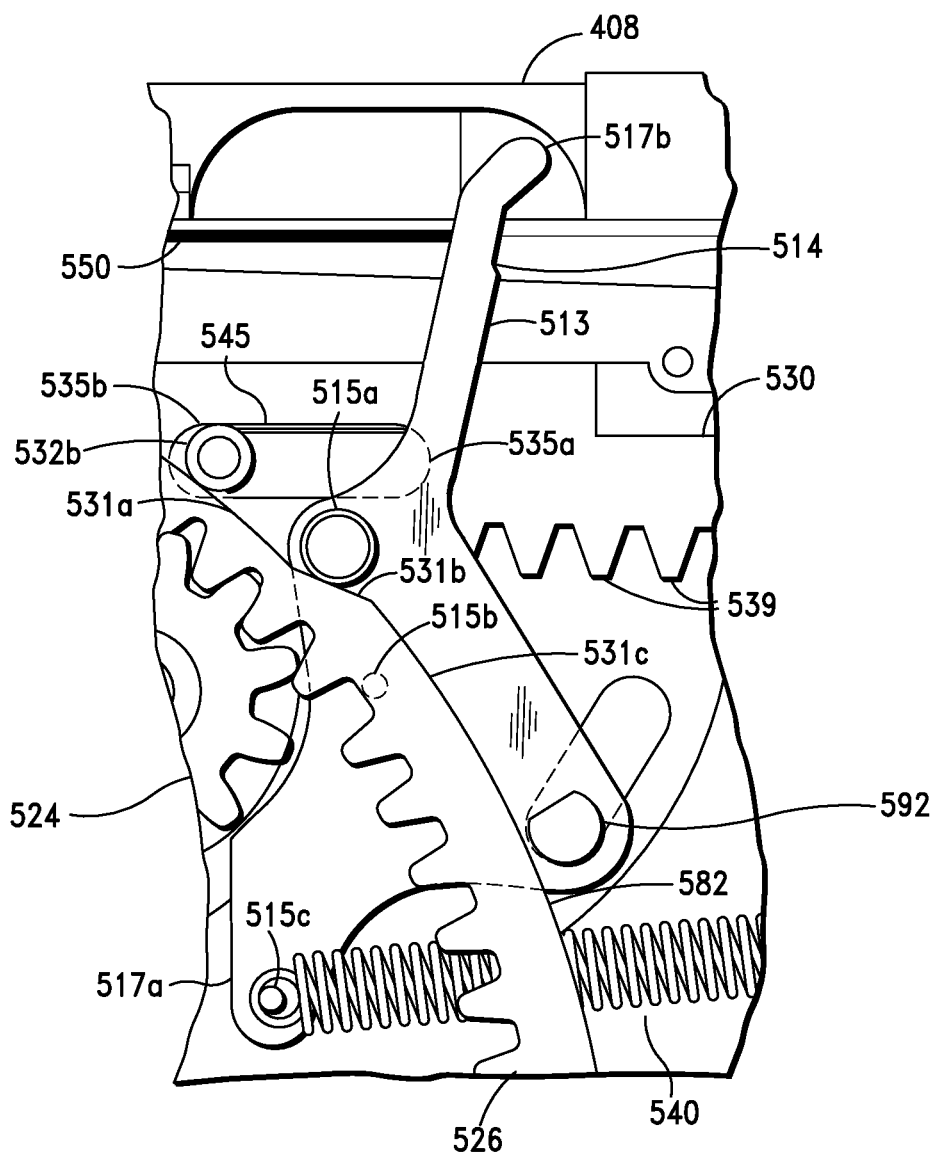
FIG. 34 is a partial side plan view of the suture passing device shown in FIG. 31A, showing a stage of the suture control system during actuation of the device control system, in accordance with the invention.

During the noted translation (or movement) of the pin 515a of the capture lever 514 along outer ring gear surface 582 of the trigger arm/ring gear 526, the pin 515a provides three (3) distinct stages of capture lever 514 articulation: (i) an initial stage, which is illustrated in FIG. 33, wherein the pin 515a traverses over the first region 531a of the outer ring gear surface 582 during initial articulation of the trigger 506 (e.g., rotation from ~0°-8.0°), wherein rotational articulation of the capture lever 514 is not induced (i.e., suture control system 513 is in dwell), (ii) a second stage, which is illustrated in FIG. 34, wherein the pin 515a traverses over the second region 531b of the outer ring gear surface 582 during further articulation of the trigger 506 (e.g., rotation from ~8.0°-11.5°), wherein the trigger arm/ring gear 526 induces rotation of the capture lever 514 (i.e., in a clockwise direction) and, thereby, retraction of ribbon 550 engaged thereto toward the proximal end 501a of the device body 502, and (iii) a third stage, wherein the pin 515a traverses over the third region 531c of the outer ring gear surface 582 during further articulation of the trigger 506 (e.g., rotation>11.5°), wherein further rotation of the capture lever 514 is not induced and the capture lever 514 and, thereby, suture capture ribbon 550 engaged thereto are in a static state in the retracted position.

In a preferred embodiment, the distal end 517b of capture lever 514 is similarly sized and configured to abut tabs 442a, 442b disposed on the bottom surface of the suture control switch 408 and similarly cooperate therewith.

As described in detail above, suture control switch 408 facilitates the above discussed ribbon engagement modes of the invention: (i) the "auto-engagement" mode and (ii) the "no-engagement" mode.

Referring again to FIG. 31A, in a preferred embodiment, the suture passing device 500 further comprises a suture release tab 590, which, as discussed in detail below, is adapted to cooperate with the capture lever 514 and, thereby, suture control system 513.

As illustrated in FIG. 31A, in a preferred embodiment, the suture release tab 590 is disposed externally on the device body 502 to facilitate easy access thereto by an operator.

As illustrated in FIG. 32, the suture release tab 590 is coupled to capture lever 514 via pin 592.

According to the invention, in a preferred embodiment, actuation of the suture release tab 590 by a manual force on the tab 590 in a direction denoted by "$F_1$" transitions the tab 590 from a default first tab position, which is illustrated in FIG. 31B, to a second tab position, which is illustrated in FIG. 31C, rotates the capture lever 514 and, thereby, translates the suture capture ribbon 550 engaged thereto into the retracted position, i.e., toward the proximal end 502a of the device frame 503 (and, hence, proximal end 473a of the jaw mechanism 460).

Actuation of the suture release tab 590 can thus be used by an operator to selectively disengage the suture capture ribbon 550 from suture 71 and release suture 71 from the distal wall 477 of the top jaw member window 470 when disposed therein.

Control of a suture, i.e., ensnarement, retainment and release, can thus also be effectuated by the multifunction actuator 505 via simple rotational articulation of the trigger 506.

In this embodiment, release of a suture 71 can also be readily effectuated by an operator by manual actuation of an external suture release tab 590.

Needle Articulation

In a preferred embodiment, the suture passing system 500 similarly further comprises a needle articulation system 541, which is also adapted to cooperate with the multifunction actuation system 505 to control articulation of the system needle, in this instance, needle 170.

As further illustrated in FIG. 32, in addition to needle 170, the suture passing device 500 comprises needle rack 530, needle support tube 518, which is similarly sized and configured to receive the needle 170 therein, and proximal and distal needle holders 532a, 532b, which are coupled to the needle support tube 518 and needle 170.

In a preferred embodiment, the needle rack 530 is similarly sized and configured to be disposed in and slidably translate within an upper internal compartment 505b of the device frame 503. As additionally illustrated in FIG. 33, the needle rack 530 further comprises a plurality of teeth 539 on the proximal end 533a of the rack 530, which are also sized and configured to cooperate with the teeth 525 on the pinion gear 524.

As further illustrated in FIG. 32, the needle rack 430 further comprises a needle rack slot 545 that is sized and configured to receive the distal needle holder 532b, whereby the distal needle holder 532b is similarly allowed to slidably translate therein and provide a needle articulation system dwell.

In a preferred embodiment, the proximal needle holder 532a is coupled to the needle support tube 518 and is positioned in the upper internal compartment 505b of the frame 503, whereby, upon rotational articulation of the trigger 506 toward the handle 504 and, thereby, linear translation of the needle rack 530 (and, thereby, needle support tube 518 and needle 170), the proximal needle holder 532a similarly abuts a proximal interior wall 505i of the device frame 503 and functions as a positive stop for the needle support tube 518, and, hence, needle translation.

As further illustrated in FIG. 32, in a preferred embodiment, the proximal needle holder 532a is similarly coupled to a needle assembly cable 522, which is sized to be drawn across two (2) pulley members 520a, 520b and coupled to a return spring 595 that provides tension to retract the needle 170 to a default retracted position when the trigger 506 is released from a fully actuated position.

In a preferred embodiment, during rotational articulation of the trigger 506, i.e., toward the handle 504, the needle rack 530 and, thereby, needle support tube 518 (and, hence, needle 170 disposed therein) similarly remain stationary (the needle 170 being in a default retracted position within the needle support tube 518) until the distal needle holder 532b abuts a proximal surface 535a of the needle rack slot 545, and, thereafter, during further rotational articulation of the trigger 506, needle rack 530 and, thereby, needle support tube 518 advance toward the distal end 502b of the device frame 503 and the needle 170 similarly advances out of the elongated shaft 510.

In a preferred embodiment, during rotational articulation of the trigger 506 away from the handle 504, i.e., upon release of the trigger 506, the needle rack 530 and, thereby, needle support tube 518 and needle 170 similarly advance toward the proximal end 502a of the device frame 503 and the needle 170 retracts into the elongated shaft 510.

According to the invention, articulation of the needle 170, i.e., translation and positioning thereof, is thus similarly provided by the multifunction actuation system 505 via simple rotational articulation of the trigger 506.

According to the invention, the multifunction actuation system 505 and, hence, suture passing device 500 is similarly adapted to sequentially (i) articulate and position the system jaw mechanism, in this instance, jaw mechanism 460, (ii) control the ensnarement, retainment and release of a suture, and (iii) articulate and position the system needle, in this instance, needle 170 during continuous rotational articulation of the trigger 506 from a default position to a fully actuated position, and sequentially provide the same functions in reverse order during continuous rotational articulation of the trigger 506 from the fully actuated position to the default position, as also set forth in FIG. 30.

As also indicated above, the suture passing device 500 is further adapted to manually effectuate ribbon 550 articulation and, thereby, suture 71 release via simple actuation of an external suture release tab 590, which is readily accessible to an operator.

Figure 35A:
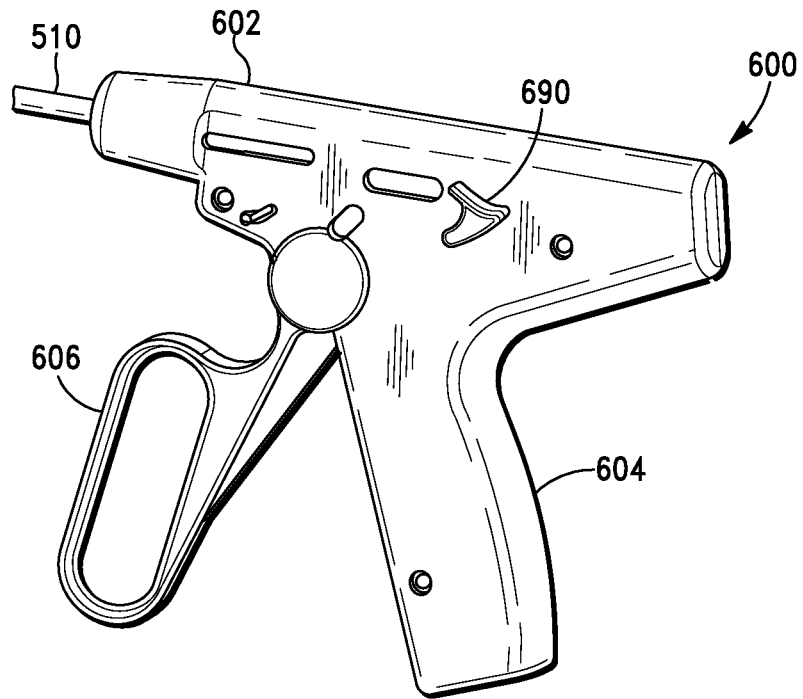
FIG. 35A is a perspective view of yet another embodiment of the suture passing device, showing a manual suture release tab, in accordance with the invention.
Figure 35B:
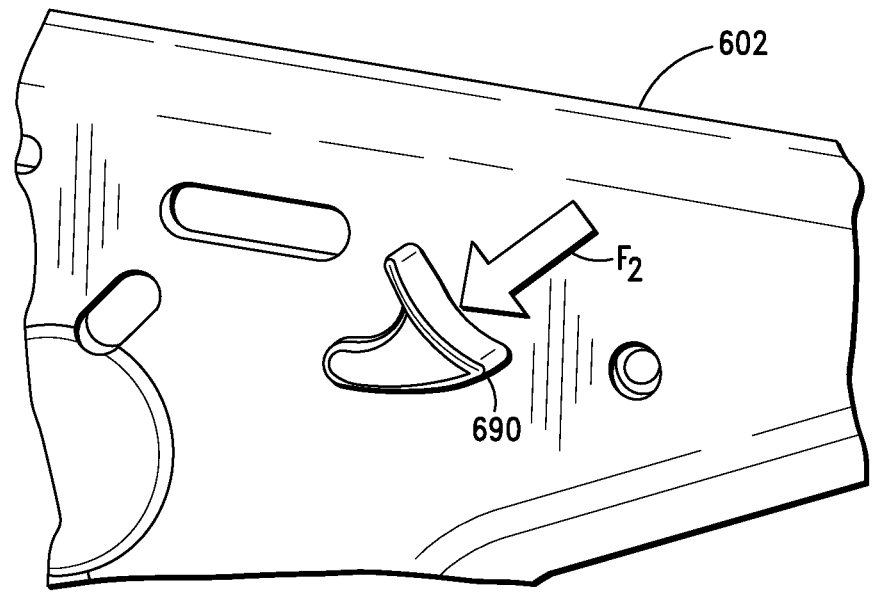
FIG. 35B is a partial perspective view of the suture passing device shown in FIG. 35A, showing the manual suture release tab in a suture release position, in accordance with the invention.

Referring now to FIGS. 35A and 35B, there is shown yet another embodiment of a suture passing device of the invention (denoted "600").

As illustrated in FIGS. 35A and 35B, the device similarly comprises a housing 602, handle 604 and the elongated member 510. According to the invention, the device 600 also comprises the jaw mechanism 460, needle assembly and suture retaining ribbon 550 of device 500, discussed above.

In a preferred embodiment, the device 600 also similarly comprises the multifunction actuation system 505, and, as reflected in FIG. 36, the jaw articulation system 544 and needle articulation system 541 of suture passing device 500 discussed above.

As further illustrated in FIGS. 35A and 35B, the device 600 does not include the suture control switch 408 (and, hence, functions and features associated therewith).

As discussed in detail below, in this embodiment, control of suture engagement and release is provided by a manual suture release system.

As illustrated in FIGS. 35A and 35B, the manual release system comprises an external suture release tab 690, which is similarly disposed on the device housing 602, whereby the tab 690 is readily accessible by an operator (i.e., easily actuated by an operator's thumb).

In a preferred embodiment, the suture retaining ribbon 550 is similarly fully advanced through the elongated shaft (denoted 510 in this embodiment), into and through the ribbon slot 454 of the top jaw member 462, and across the jaw member window 470, whereby suture access therein is abated.

In a preferred embodiment, the manual suture release system is configured and adapted to cooperate with the suture capture ribbon 550, whereby, upon manual actuation of the suture release tab 690 via application of a force in a downward direction, as denoted by arrow "$F_2$" (and holding the tab 690 in the actuated position), and rotational articulation of the trigger 606 toward the handle 604, the suture retaining ribbon 550 retracts, allowing access of a suture into the jaw member window 470.

According to the invention, the manual suture release system is also configured and adapted to retract the suture capture ribbon 550 and allow access of a suture into the jaw member window 470 upon "simultaneous" manual actuation of the suture release tab 690 and rotational articulation of the trigger 606 toward the handle 604.

In a preferred embodiment, upon a simple release of the tab 690, the suture retaining ribbon 550 extends to its default position and engages and retains the suture in the recess or opening in the distal wall 477 of the jaw member window 470.

Upon manual actuation of the suture release tab 690 thereafter and rotational articulation of the trigger 606 toward the handle 604, the suture retaining ribbon 550 can again be retracted to effectuate release of the suture from the distal wall 477 of the jaw member window 470.

Suture passing device 600, thus, effectuates simple suture control, i.e., engagement and release, through simple one-handed operation via two (2) actuators.

As will readily be appreciated by one having ordinary skill in the art, the present invention provides numerous advantages compared to prior art systems and methods for passing suture through biological tissue. Among the advantages are the following:

The provision of suture passing systems that can be readily employed to effectively approximate, ligate, fixate and/or close biological tissue;

The provision of suture passing systems that provide an enhanced degree of control of tissue engagement, needle articulation and suture retention by an operator with minimal complexity;

The provision of suture passing systems that provide synchronized control of tissue engagement, needle articulation and suture retention with a single motion of a hand actuator;

The provision of suture passing systems that include independent manual means for releasing a tissue after retainment;

The provision of suture passing systems that facilitate suture passage into and through a myriad of soft tissue types;

The provision of suture passing systems that facilitate suture passage into and through biological tissue structures having a wide range of thicknesses;

The provision of suture passing systems that provide enhanced suture manipulation in a surgical site;

The provision of suture passing systems that can be readily employed to endure multiple use cycles with limited impact on suture passing efficacy;

- The provision of suture passing systems that can be readily employed to enable antegrade and retrograde passing of suture during endoscopic surgical procedures;
- The provision of suture passing systems that can be readily employed to enable an operator to generate high tensile strength stitch patterns during an endoscopic procedure, such as a modified Mason-Allen stitch;
- The provision of suture passing systems that can be readily employed to pass suture without collateral damage to extraneous soft tissue and bone structures; and
- The provision of suture passing systems that reduce the time required to conduct suturing procedures and, thereby, attendant risks to a patient.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A suture passing device, comprising:
a jaw mechanism adapted to grasp biological tissue and engage a suture, said jaw mechanism comprising top and bottom jaw members, said top jaw member adapted to axially articulate with respect to said bottom jaw member;
a needle assembly comprising a needle, said needle comprising a tissue piercing distal end configured to releasably engage a suture;
a jaw articulation system adapted to induce and control said axial articulation of said top jaw member with respect to said bottom jaw member;
a suture control system adapted to control access of said suture into said jaw mechanism and said engagement of said suture by said jaw mechanism, said suture control system further adapted to control release of said suture by said jaw mechanism after said engagement by said jaw mechanism;
a needle articulation system adapted to induce and control articulation of said needle and, thereby, said needle engagement to said suture; and
a multifunction actuation system, said multifunction actuation system comprising an actuation trigger, said actuation trigger adapted to rotationally articulate from a default position to a fully actuated position, said default position comprising 0° rotation of said actuation trigger,
said multifunction actuation system adapted to control said jaw articulation system, said suture control system and said needle articulation system,
said control of said jaw articulation system, said suture control system and said needle articulation system comprising synchronized said axial articulation of said top jaw member with respect to said bottom jaw member, said access of said suture into said jaw mechanism, and said articulation of said needle during a first single continuous rotational articulation of said actuation trigger, said first single continuous rotational articulation of said actuation trigger comprising rotational articulation from said default position to said fully actuated position.

2. The device of claim 1, wherein said control of said jaw articulation system, said suture control system and said needle articulation system further comprises synchronized said articulation of said needle, said suture engagement by said jaw mechanism, and said axial articulation of said top jaw member with respect to said bottom jaw member during a second single continuous rotational articulation of said actuation trigger, said second single continuous rotational articulation of said actuation trigger comprising rotational articulation from said fully actuated position to said default position.

3. The device of claim 1, wherein said needle assembly is in communication with said jaw mechanism and adapted to cooperate with said jaw mechanism.

4. The device of claim 1, wherein said device further comprises an elongated tubular member in communication with said jaw mechanism and said needle assembly, said elongated tubular member comprising an internal lumen configured to receive said needle therein and advance said needle therefrom when said needle is said articulated by said multifunction actuation system.

5. The device of claim 4, wherein said top jaw member of said jaw mechanism comprises a ribbon slot and jaw member window adapted to receive said suture therein, said ribbon slot in communication with said elongated tubular member.

6. The device of claim 5, wherein said suture control system comprises a suture retaining ribbon in communication with said multifunction actuation system, said suture retaining ribbon comprising first and second configurations, said first configuration comprising a default extended configuration and said second configuration comprising a retracted configuration.

7. The device of claim 6, wherein said suture retaining ribbon is adapted to transition from said default extended configuration to said retracted configuration, and from said retracted configuration to said default extended configuration.

8. The device of claim 7, wherein said suture retaining ribbon extends from said multifunction actuation system, through said elongated tubular member, through said ribbon slot and, when said suture retaining ribbon is in said default extended configuration, over said jaw member window in said top jaw member.

9. The device of claim 7, wherein, when said suture retaining ribbon is in said extended configuration, said suture is restricted from entering said jaw member window.

10. The device of claim 9, wherein, during said first single continuous rotational articulation of said actuation trigger, said suture retaining ribbon said transitions from said default extended configuration to said retracted configuration, whereby access to said jaw member window by said suture is provided.

11. The device of claim 10, wherein, during said second single continuous rotational articulation of said actuation trigger, said suture retaining ribbon said transitions from said retracted configuration to said default extended configuration, whereby, when said suture is disposed in said jaw member window, said suture retaining ribbon engages said suture and retains said suture in said jaw member window.

12. The device of claim 11, wherein said multifunction actuation system further comprises a suture mode switch adapted to selectively provide multiple ribbon/suture engagement modes.

13. The device of claim 12, wherein said multiple ribbon/suture engagement modes comprise an auto-engagement mode, wherein said suture retaining ribbon is allowed to said transition from said retracted configuration to said default extended configuration, whereby, when said suture is disposed in said jaw member window, said suture retaining ribbon engages said suture during said second single continuous rotational articulation of said actuation trigger, and during said first single continuous rotational articulation of said actuation trigger said suture retaining ribbon is allowed to said transition from said default extended configuration to said retracted configuration, whereby said suture retaining ribbon disengages from said suture.

14. The device of claim 13, wherein said multiple ribbon/suture engagement modes comprise a no-engagement mode, wherein said suture retaining ribbon is maintained in said retracted configuration, whereby, when said suture is disposed in said jaw member window, said suture retaining ribbon does not transition from said retracted configuration to said default extended configuration and, thereby engage said suture during said second single continuous rotational articulation of said trigger.

15. The device of claim 13, wherein said multifunction actuation system further comprises a suture release switch adapted to release said suture from said jaw member window when said engaged by said suture retaining ribbon.

* * * * *